US008323956B2

(12) United States Patent
Reardon et al.

(10) Patent No.: US 8,323,956 B2
(45) Date of Patent: Dec. 4, 2012

(54) DISTAL TIP OF BIOSENSOR TRANSDUCER COMPRISING ENZYME FOR DEAMINATION

(75) Inventors: Kenneth F. Reardon, Fort Collins, CO (US); Lawrence Philip Wackett, St. Paul, MN (US)

(73) Assignee: Colorado State University Research Foundation, Fort Collins, CO (US)

( * ) Notice: Subject to any disclaimer, the term of this patent is extended or adjusted under 35 U.S.C. 154(b) by 340 days.

(21) Appl. No.: 12/358,140

(22) Filed: Jan. 22, 2009

(65) Prior Publication Data

US 2009/0221014 A1 Sep. 3, 2009

Related U.S. Application Data

(63) Continuation-in-part of application No. 12/100,308, filed on Apr. 9, 2008, which is a continuation-in-part of application No. 10/478,822, filed as application No. PCT/US02/17407 on Jun. 1, 2002, now Pat. No. 7,381,538.

(60) Provisional application No. 60/922,496, filed on Apr. 9, 2007, provisional application No. 61/024,453, filed on Jan. 29, 2008, provisional application No. 60/295,211, filed on Jun. 1, 2001.

(51) Int. Cl.
C12M 1/34 (2006.01)
C12Q 1/34 (2006.01)
C12Q 1/26 (2006.01)
C12N 11/02 (2006.01)
C12N 11/08 (2006.01)
C12N 11/04 (2006.01)

(52) U.S. Cl. ......... 435/287.1; 435/18; 435/25; 435/177; 435/180; 435/182

(58) Field of Classification Search .................. None
See application file for complete search history.

(56) References Cited

U.S. PATENT DOCUMENTS

| | | | |
|---|---|---|---|
| 4,739,380 A | 4/1988 | Lauks et al. | |
| 5,152,758 A | 10/1992 | Kaetsu et al. | |
| 5,156,810 A | 10/1992 | Ribi | |
| 5,177,012 A | 1/1993 | Kim et al. | |
| 5,250,439 A | 10/1993 | Musho et al. | |
| 5,508,193 A | 4/1996 | Mandelbaum et al. | |
| 5,541,057 A | 7/1996 | Bogart et al. | |
| 5,543,317 A | 8/1996 | Shields et al. | |
| 5,629,214 A | 5/1997 | Crosby | |
| 5,698,083 A | 12/1997 | Glass | |
| 5,798,030 A | 8/1998 | Raguse et al. | |
| 5,837,196 A | 11/1998 | Pinkel et al. | |
| 5,837,454 A | 11/1998 | Cozzette et al. | |
| 5,972,199 A | 10/1999 | Heller et al. | |
| 5,972,638 A | 10/1999 | Burlage et al. | |
| 6,022,748 A | 2/2000 | Charych et al. | |
| 6,060,327 A | 5/2000 | Keen | |
| 6,100,080 A * | 8/2000 | Johansen | 435/264 |
| 6,159,681 A | 12/2000 | Zebala | |
| 6,265,201 B1 | 7/2001 | Wackett et al. | |
| 6,271,015 B1 * | 8/2001 | Gilula et al. | 435/228 |
| 6,284,522 B1 | 9/2001 | Wackett et al. | |
| 6,291,200 B1 | 9/2001 | LeJeune et al. | |
| 6,369,299 B1 | 4/2002 | Sadowsky et al. | |
| 6,825,001 B2 | 11/2004 | Wackett et al. | |
| 7,381,538 B2 * | 6/2008 | Reardon et al. | 435/23 |
| 7,595,181 B2 * | 9/2009 | Gruning et al. | 435/197 |
| 7,709,221 B2 | 5/2010 | Rose et al. | |
| 2004/0265811 A1 | 12/2004 | Reardon et al. | |
| 2006/0275855 A1 * | 12/2006 | Blackburn et al. | 435/15 |

FOREIGN PATENT DOCUMENTS

WO WO 03/025892 12/1993

OTHER PUBLICATIONS

PCT/US2009/040121, International Search Report & Written Opinion mailed Jul. 14, 2009, 8 pages.
Adachi, K., et al; Purification and properties of homogentisate oxygenase from *Pseudomonas fluorescens*. Biochim. Biophys. Acta 118 (1966) 88-97.
Aldridge, W.N.; Serum esterases. I. Two types of esterase (A and B) hydrolysing p-nitrophenyl acetate, propionate and butyrate and a method for their determination. Biochem. J. 53 (1953) 110-117.
Amitai, G. et al.; Enhanced stereoselective hydrolysis of toxic organophosphates by directly evolved variants of mammalian serum paraoxonase; FEBS Journal 273 (2006) pp. 1906-1919.
Augusteyn, R.C., et al; On the homology of the active-site peptides of liver Carboxylesterases. Biochim. Biophys. Acta 171 (1969) 128-137.
Bertoni, G., et al; "Cloning of the Genes for and Characterization of the Early Stages of Toluene and o-Xylene Catabolism in *Pseudomonas stutzeri* OX1," Applied and Environmental Microbiology, 1996, 62(10): pp. 3704-3711.
Bertoni, G., et al; "Analysis of the Gene Cluster Encoding Toluene/o-Xylene Monoxygenase from *Pseudomonas stutzeri* OX1," Applied and Environmental Microbiology, 1998. 64(10): pp. 3626-3632.
Buchinger, P.J. et al.; Characteristics of Microbial Assay for the Detection of Halogenated Hydrocarbons Using Cells of an Actinomycete-like Organism as a Biological Component; Acta Biotechnol. 17 (1997) 2, 123-130.
Byrne, A.M., et al; "Sequence Analysis of the Gene Cluster Encoding Toluene-3-monooxygenase from *Pseudomonas pickettii* PK01," Gene, 1995. 154: pp. 65-70.
Cardini, G. & Jurtshuk, P. The enzymatic hydroxylation of n-octane by *Corynebacterium* sp. strain 7E1C. J. Biol. Chem. 245 (1970) 2789-2796.

(Continued)

*Primary Examiner* — David Naff
(74) *Attorney, Agent, or Firm* — Lathrop & Gage LLP

(57) ABSTRACT

Enzymatic biosensors and methods of producing distal tips for biosensor transducers for use in detecting one or more analytes selected from organic compounds susceptible to dehalogenation, organic compounds susceptible to oxygenation, organic compounds susceptible to deamination, organosulfate compounds susceptible to hydrolysis, and organophosphate compounds susceptible to hydrolysis are disclosed herein, as well as biosensor arrays, methods of detecting and quantifying analytes within a mixture, and devices and methods for delivering reagents to enzymes disposed within the distal tip of a biosensor.

20 Claims, 10 Drawing Sheets

OTHER PUBLICATIONS

Chang, K. H., et al; Isolation and characterization of the three polypeptide components of 4-chlorobenzoate dehalogenase from *Pseudomonas* sp. strain CBS-3. Biochemistry 31 (1992) 5605-5610.

Chopra, I. J. & Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97.

Colby, J. et al; The soluble methane mono-oxygenase of *Methylococcus capsulatus* (Bath). Its ability to oxygenate n-alkanes, n-alkenes, ethers, and alicyclic, aromatic and heterocyclic compounds. Biochem. J. 165 (1977) 395-402.

Crooks, G. P. & Copley, S. D.; Purification and characterization of 4-chlorobenzoyl CoA dehalogenase from *Arthrobacter* sp. strain 4-CB1. Biochemistry, 33 (1994) 11645-11649.

de Souza, M. L., et al; Atrazine chlorohydrolase from *Pseudomonas* sp. strain ADP: gene sequence, enzyme purification, and protein characterization. J. Bacteriol. 178 (1996) 4894-4900.

de Souza, M. L. et al; Cloning, characterization, and expression of a gene region from *Pseudomonas* sp. strain ADP involved in the dechlorination of atrazine. Appl. Environ. Microbiol. 61 (1995) 3373-3378.

Dodgson, K.S., et al; Studies on sulphatases. 13. The hydrolysis of substituted phenyl sulphates by the arylsulphatase of *Alcaligenes metacaligenes*. Biochem. J. 64 (1956) 216-221.

Ensley, B.D. & Gibson, D.T. Naphthalene dioxygenase: purification and properties of a terminal oxygenase component. J. Bacteriol. 155 (1983) 505-511.

Fetzner, S., et al; Degradation of 2-chlorobenzoate by *Pseudomonas cepacia* 2CBS. Biol. Chem. Hoppe-Seyler 370 (1989) 1173-1182.

Fujisawa, H. & Hayaishi, O.; Protocatechuate 3,4-dioxygenase. I. Crystallization and characterization. J. Biol. Chem. 243 (1968) 2673-2681.

Goldman, P. & Milne, G. W. A.; Carbon-fluorine bond cleavage. II. Studies on the mechanism of the defluorination of fluoroacetate. J. Biol. Chem. 241 (1966) 5557-5559.

Goldman, P., et al.; Carbon-halogen bond cleavage. 3. Studies on bacterial halidohydrolases. J. Biol. Chem. 243 (1968) 428-434.

Goldman, P.; The enzymatic cleavage of the carbon-fluorine bond in fluoroacetate. J. Biol. Chem. 240 (1965) 3434-3438.

Goswam A., et al.; Inhibition by coumadin anticoagulants of enzymatic outer ring monodeiodination of iodothyronines. Biochem. Biophys. Res. Commun. 104 (1982) 1231-1238.

Hayaishi, O. & Sutton, W.B. Enzymatic oxygen fixation into acetate concomitant with the enzymatic decarboxylation of L-lactate. J. Am. Chem. Soc. 79 (1957) 4809-4810.

Heppel, L. A. & Porterfield, V. T. Enzymatic dehalogenation of certain brominated and chlorinated compounds. *J. Biol. Chem.* 176 (1948) 763-769.

Hosokawa, K. & Stanier, R.Y. Crystallization and properties of p-hydroxybenzoate hydroxylase from *Pseudomonas putida*. J. Biol. Chem. 241 (1966) 2453-2460.

Junker, F., et al; Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. Biochem. J. 300 (1994) 429-436.

Keuning, S., Janssen, D. B. & Witholt, B.; Purification and characterization of hydrolytic haloalkane dehalogenase from *Xanthobacter autotrophicus* GJ10; J. Bacteriol. 163 (1985) 635-639.

Kohler-Staub, D. & Leisinger, T.; Dichloromethane dehalogenase of *Hyphomicrobium* sp. strain DM2. J. Bacteriol. 162 (1985) 676-681.

Kumagai, H., et al; S-Carboxymethylcysteine synthase from *Escherichia coli*. Agric. Biol. Chem. 53 (1989) 2481-2487.

Lipke, H. & Kearns, C. W.; DDT dechlorinase. I. Isolation, chemical properties, and spectrophotometric assay. J. Biol. Chem. 234 (1959) 2123-2128.

Lipke, H. & Kearns, C. W.; DDT dechlorinase. II. Substrate and cofactor specificity. J. Biol. Chem. 234 (1959) 2129-2132.

Moriguchi, M., et al.; Dehalogenation and deamination of 1-2-amino-4-chloro-4-pentenoic acid by *Proteus mirabilis*. Agric. Biol. Chem. 51 (1987) 3295.

Motosugi, M., et al.; Preparation and properties of 2-halo acid dehalogenase from *Pseudomonas putida*. Agric. Biol. Chem. 46 (1982) 837-838.

Muller, R., et al.; Incorporation of [18O]water into 4-hydroxybenzoic acid in the reaction of 4-chlorobenzoate dehalogenase from *Pseudomonas* sp. CBS 3. Biochem. Biophys. Res. Commun. 124 (1984) 178-182.

Muller, C. et al.; Multicomponent fiberoptical biosensor for use in hemodialysis monitoring; SPIE Biomedical Fiber Optic Instrumentation; vol. 2131; pp. 555-562 (Jul. 1994).

Nagasawa, T., et al.; Physiological comparison of D-cysteine desulfhydrase of *Escherichia coli* with 3-chloro-D-alanine dehydrochlorinase of *Pseudomonas putida* CR 1-1. Arch. Microbiol. 149 (1988) 413-416.

Nakagawa, H. and Takeda, Y. Phenol hydroxylase. Biochim. Biophys. Acta 62 (1962) 423-426.

Nordlund, I. et al; "Complete nucleotide sequence and polypeptide analysis of multicomponent phenol hydroxylase from *Pseudomonas* sp. strain CF600," Journal of Bacteriology, 1990. 172: pp. 6826-6833.

Pikus, J.D., et al; "Recombinant Toluene-4-Monoxygenase: Catalytic and Mossbauer Studies of the Purified Diiron and Rieski Components of a Four-Protein Complex," Biochemistry, 1996. 35: pp. 9106-9119.

Ramanathan, M. & Simonian, A.L.; Array biosensor based on enzyme kinetics monitoring by fluorescence spectroscopy: Application for neurotoxins detection; Biosensors and Bioelectronics 23 (2007) pp. 3001-3007.

Renganathan, V. Possible involvement of toluene-2,3-dioxygenase in defluorination of 3-fluoro-substituted benzenes by toluene-degrading *Pseudomonas* sp. strain T-12. Appl. Exp. Microbiol. 55 (1989) 330-334.

Rosenzwieg, A.C., et al. "Geometry of the Soluble Methane Monoxygenase Catalytic Diiron Center in Two Oxidation States," Chemistry and Biology, 1995. 2(6): pp. 409-418.

Schenk, T., et al.; Enzymatic dehalogenation of pentachlorophenol by extracts from *Arthrobacter* sp. strain ATCC 33790. J. Bacteriol. 171 (1989) 5487-5491.

Scholtz, R., et al.; Characterization of 1-chlorohexane halidohydrolase, a dehalogenase of wide substrate range from an *Arthrobacter* sp. J. Bacteriol. 169 (1987) 5016-5021.

Simonian, AL, et al.; FET-Based Biosensors for the Direct Detection of Organophosphate Neurotoxins; Electroanalysis 2004; 16, No. 22; pp. 1896-1906.

Smallridge, R. C., et al. "3',5'-Diiodothyronine to 3'-monoiodothyronine conversion in the fed and fasted rat: enzyme characteristics and evidence for two distinct 5'-deiodinases" Endocrinology 108 (1981) 2336-2345.

Suzuki, K., Takemori, S. and Katagiri, M. Mechanism of the salicylate hydroxylase reaction. IV. Fluorimetric analysis of the complex formation. Biochim. Biophys. Acta 191 (1969) 77-85.

Yamada, H., et al; Synthesis of D-cysteine from 3-chloro-D-alanine and hydrogen sulfide by 3-chloro-D-alanine hydrogen chloride-lyase (deaminating) of *Pseudomonas putida*. Biochem. Biophys. Res. Commun. 100 (1981) 1104-1110.

Yen, K.-M., "Construction of Cloning Cartridges for Development of Expression Vectors in Gram-Negative Bacteria," J. Bacteriol., 1991. 173(17): pp. 5328-5335.

Moorefield, H. H. Purification of DDT-dehydrochlorinase from resistant houseflies. Contr. Boyce Thompson Inst. 18 (1956) 303-310.

Hayaishi, O. and Sutton, W.B. Enzymatic oxygen fixation into acetate concomitant with the enzymatic decarboxylation of L-lactate. J. Am. Chem. Soc. 79 (1957) 4809-4810.

Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). Acta Chem. Scand. 8 (1954) 753-761.

Cardy, D.L.N., V. Laidler, G.P.C. Salmond, and J.C. Murrell, "Molecular Analysis of the Methane Monooxygenase (MMO) Gene Cluster of *Methylosinus trichosporium* OB3b," Molecular Microbiology, 1991. 5(2): pp. 335-342.

Fox, B.G., et al., "Methane Monooxygenase from *Methylosinus trichosporium* OB3b," Journal of Biological Chemistry, 1989. 264(17): pp. 10023-10033.

Stainthorpe, A.C., et al., "The Methane Monooxygenase Gene Cluster of *Methylococcus capsulatus* (Bath)," Gene, 1990. 91: pp. 27-34.

McClay, K., B.G. Fox, and R.J. Steffan, "Chloroform Mineralization by Toluene-Oxidizing Bacteria," Applied and Environmental Microbiology, 1996. 62(8): pp. 2716-2722.

Nordlund, I., et al, "Complete nucleotide sequence and polypeptide analysis of multicomponent phenol hydroxylase from *Pseudomonas* strain CF600," Journal of Bacteriology, 1990. 172: pp. 6826-6833.

Ziegler, D.M. and Pettit, F.H. Microsomal oxidases. I. The isolation and dialkylarylamine oxygenase activity of pork liver microsomes. Biochemistry 5 (1966) 2932-2938.

Yokota, T., et al.; Purification and properties of haloalkane dehalogenase from *Corynebacterium* sp. strain m15-3. J. Bacteriol. 169 (1987) 4049-4054.

PCT/US02/17407 International Search Report; mailed Sep. 24, 2003; 2 pages.

PCT/US02/17407 International Preliminary Examination Report; Mar. 4, 2005; 4 pages.

U.S. Appl. No. 10/478,822; Restriction Requirement mailed Jan. 12, 2007; 4 pages.

U.S. Appl. No. 10/478,822; Response to Restriction Requirement, filed Feb. 12, 2007; 6 pages.

U.S. Appl. No. 10/478,822; Office Action mailed May 17, 2007; 13 pages.

U.S. Appl. No. 10/478,822; Response to Office Action, filed Aug. 17, 2007; 79 pages.

U.S. Appl. No. 10/478,822; Office Action mailed Oct. 31, 2007; 6 pages.

U.S. Appl. No. 10/478,822; Response to Office Action, filed Dec. 28, 2007; 10 pages.

U.S. Appl. No. 10/478,822; Notice of Allowance mailed Feb. 13, 2008; 3 pages.

U.S. Appl. No. 10/478,822; Issue Notification, filed May 14, 2008; 1 page.

U.S. Appl. No. 12/100,308, Advisory Action mailed Sep. 23, 2011, 3 pages.

U.S. Appl. No. 12/100,308, Response to Office Action, filed Sep. 13, 2011, 12 pages.

U.S. Appl. No. 12/100,308, Office Action mailed Jul. 13, 2011, 9 pages.

U.S. Appl. No. 12/100,308, Office Action mailed Feb. 4, 2011, 12 pages.

U.S. Appl. No. 12/100,308, Response to Office Action, filed Apr. 8, 2011, 28 pages.

Mulchandani, A. et al.; Biosensor for Direct Determination of Organophosphate Nerve Agents Using Recombinant *Escherichia coli* with Surface-Expressed Organophosphorus Hydrolase. 2. Fiber-Optic Microbial Biosensor. Analytical Chemistry 1998 70 (23), 5042-5046.

U.S. Appl. No. 12/100,308, Response to Office Action filed Nov. 14, 2011, 39 pages.

* cited by examiner

Enzyme Membrane    pH-FET

DISTAL TIP OF BIOSENSOR TRANSDUCER COMPRISING ENZYME FOR DEAMINATION

RELATED APPLICATIONS

This application is a continuation-in-part of U.S. patent application Ser. No. 12/100,308, filed Apr. 9, 2008, which claimed the benefit of priority to U.S. Provisional Patent Application Ser. Nos. 60/922,496, filed Apr. 9, 2007, and 61/024,453, filed Jan. 29, 2008, and which was a continuation-in-part of U.S. patent application Ser. No. 10/478,822, now U.S. Pat. No. 7,381,538, which was a national phase entry under 35 U.S.C. §371 of PCT/US02/17407, filed Jun. 1, 2002, which claimed the benefit of priority to U.S. Provisional Patent Application Ser. No. 60/295,211, filed Jun. 1, 2001. Each of these applications is incorporated by reference herein.

GOVERNMENT RIGHTS

This invention was made with Government support under contract number BES-0529048 awarded by the National Science Foundation and contract number DACA71-01-C-0009 awarded by the U.S. Army Research Office. The U.S. Government has certain rights in this invention.

BACKGROUND

A biosensor contains a biological component (e.g., enzyme, antibody, DNA/RNA, aptamer) coupled to a transducer, which is typically a physical sensor, such as a microcantilever, or a chemical sensor, such as a pH electrode, that produces a signal proportional to analyte concentration. The analyte is normally detected by the biocomponent through a chemical reaction or physical binding. For example, in the case of an enzyme biosensor, a product of the enzyme-catalyzed reaction, such as oxygen, ammonia, hydrochloric acid or carbon dioxide, may be detected by an optical or electrochemical transducer.

Enzymes are preferred biocomponents because they are catalytic, specific to a particular substrate (analyte) and fast acting. Generally, enzymes for use in a biosensor may be disposed within whole cells or extracted from cells and purified. Whole cells are less expensive than purified enzymes and may provide an environment for longer enzyme stability, but cell-based biosensors typically have longer response times and less specificity to a single analyte than purified enzymes due to the presence of multiple enzymes within the cells. Whole-cell biosensors may utilize dead cells or living cells; the later may require proper control of environment and maintenance to retain their efficacy.

The use of purified enzymes in biosensors has also been explored. In D. W. Campbell, "The Development of Biosensors for the Detection of Halogenated Groundwater Contaminants," Spring 1998, Colorado State University, Fort Collins, Colo., reference is made to a pH optode featuring the reaction illustrated schematically in FIG. 2.4 of Campbell: the cleavage of halide ion $X^-$ and proton $H^+$ from a halogenated hydrocarbon by the appropriate hydrolytic dehalogenase. An earlier reference, C. Müller, F. Schubert and T. Scheper, Multicomponent fiberoptical biosensor for use in hemodialysis monitoring, SPIE Proc., Vol. 2131, Biomedical Fiber Optic Instrumentation, Los Angeles, Calif., USA (1994) ISBN 0-8194-1424-7, pp. 555-562, employed a pH optode-type biosensor limited to the use of urease as a catalyst (urea is split into ammonia & $CO_2$): the bifunctional reagent glutaraldehyde was used to bind urease directly to the head of a pH optode. These examples demonstrate the feasibility of utilizing purified enzymes in biosensors with the advantage that the enzymes are not exposed to proteases, found in whole cells, that degrade intracellular proteins. However, extraction, isolation and purification of a particular enzyme can be expensive, tedious and complicated, as well as cause the enzyme to lose a high percentage of its activity.

In addition to the particular circumstances affecting whole cells and purified enzymes discussed above, there are two important challenges to the overall development of enzyme-based biosensors. First, the resolution of similar analytes within a mixture has proven difficult. Although enzymes are generally considered specific, most have activity toward similar molecules within the same chemical family. Second, biosensors containing enzymes that require a cofactor, such as nicotinamide adenine dinucleotide (NADH), have limited lifetimes because cofactors, which are consumed during enzyme-catalyzed detection of an analyte, must be regenerated. The supply of cofactors, either through an ancillary reaction that occurs outside the cell or a metabolic process within a living cell, is non-trivial and has hindered the development of biosensors that require cofactors.

SUMMARY

The present instrumentalities advance the art and overcome the problems discussed above by providing biosensors and methods of producing distal tips for biosensor transducers for use in detecting one or more analytes selected from organic compounds susceptible to dehalogenation, organic compounds susceptible to oxygenation, organic compounds susceptible to deamination, organosulfate compounds susceptible to hydrolysis, and organophosphate compounds susceptible to hydrolysis.

In an embodiment, a distal tip of a biosensor transducer for use in detecting an organic compound susceptible to deamination includes a biocomponent comprising one or more enzymes for carrying out deamination of the organic compound.

In an embodiment, a distal tip of a biosensor transducer for use in detecting an organic compound susceptible to deamination includes a biocomponent comprising at least one enzyme selected from the group consisting of hydrolases from EC family 3.5 and lyases from EC family 4.3 for carrying out deamination of the organic compound.

In an embodiment, a distal tip of a biosensor transducer for use in detecting organic compounds includes a biocomponent comprising at least one enzyme selected from the group consisting of hydrolases from EC family 3.5 and lyases from EC family 4.3 for carrying out deamination of one organic compound; and one or more of (i) an oxygenase from EC family 1.13 for carrying out an oxidation of one organic compound, (ii) an oxygenase from EC family 1.14 for carrying out an oxidation of one organic compound, (iii) a dehalogenase for carrying out dehalogenation of one organic compound, and (iv) a hydrolase from subclass EC 3.1 for carrying out a hydrolysis of one organic compound.

In each of the embodiments above, the biocomponent is immobilized to a surface of the tip by one or more of (a) entrapment within a hydrogel; (b) entrapment within a polymeric network; (c) encapsulation; (d) covalent bonding; and (e) adsorption. The biocomponent is further stabilized to the tip by one or more of crosslinking a surface of the immobilized biocomponent, crosslinking a polymer layer to the biocomponent, adding a gel-hardening agent to the biocomponent, adding a stabilizing agent to the biocomponent, and modifying a component used to immobilize the biocomponent to the surface of the tip.

DETAILED DESCRIPTION

Figure 1:
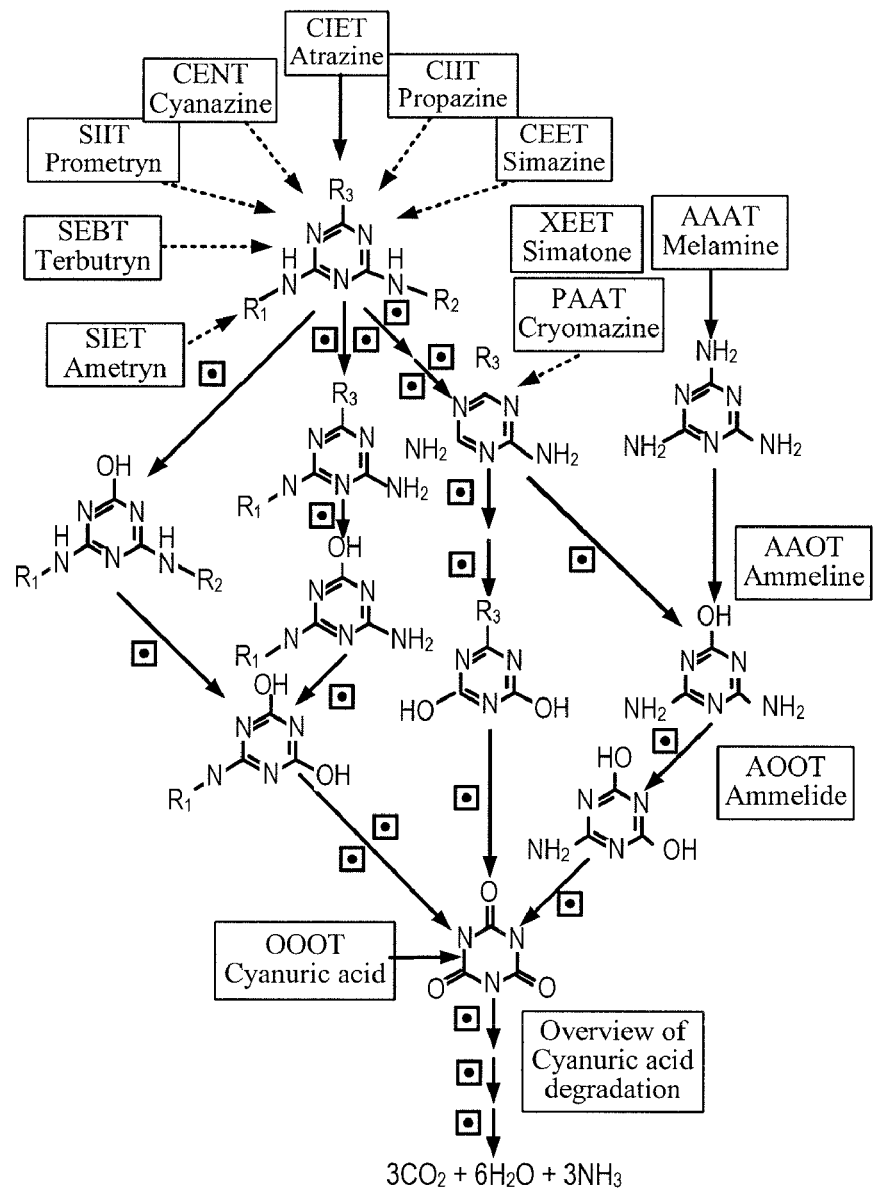
FIG. 1 is a depiction of several pathways derived from general knowledge of the degradation of atrazine.

The present technology relates to real-time, in situ, reagentless techniques for monitoring organic chemicals (pollutants, pesticides, contaminants, etc.) in soil, groundwater, drinking water, waste water, and other aqueous environments, as well as a wide variety of other applications. For example, medical uses include disposable one-way sensors (assays) for routine blood, saliva and urine testing, and in vivo sensors for monitoring crucial parameters during surgery and other procedures. In one example, the biosensor may be made small enough to be placed inside a catheter for measurements within blood vessels. Food and drink industry applications include contaminant detection, verification of product content (glucose and sucrose concentrations), monitoring of raw material conversion and evaluation of product freshness. Process control applications include monitoring reactant, product, and dissolved gas concentrations in various processes such as fermentation and microbial cell growth. Environmental monitoring applications include monitoring concentration and toxicity of contaminants (e.g., heavy metals, pesticides) in surface and groundwater, waste streams and soil. Defense and homeland security industry applications include measuring the presence of chemical warfare agents such as nerve gases and mustard gas, detection of trace vapors, explosives and drugs.

Water Contamination

Measurements of water contaminant concentrations are critical to site characterization and remediation process monitoring. However, current techniques for groundwater contaminant monitoring suffer from several problems. Measurements are expensive, slow and require removal of the sample from the site, thereby adding to the cost and altering the analyte concentration through nonlinear volume averaging and volatile losses. Currently, the primary method for monitoring groundwater involves removing a groundwater sample from a well (an average of a large volume), packaging it into several sample vials, shipping it to a laboratory and receiving the analysis weeks later.

Although analysis is traditionally performed by gas or liquid chromatography, immunoassays for contaminant measurements have recently become available. However, immunoassays still require sample removal and provide a single, time-delayed measurement. Moreover, immunoassays are not sufficiently specific for small molecules, such as toluene, benzene and chlorinated ethenes, because it is difficult to obtain antibodies for small molecules.

Food Contaminants

Melamine—a reagent in the manufacture of plastics—has recently been discovered in animal feedstock and baby formula. The presence of melamine in food is alarming because melamine is a suspected carcinogen, and, when combined with cyanuric acid, insoluble melamine cyanurate forms as kidney stones. Despite these health risks, melamine is sometimes illegally added to food products to artificially increase their protein content. The current standard method for measuring melamine, and other amine-containing compounds, in food is a gas chromatographic method that requires expensive equipment and a two-day procedure. Biosensors disclosed herein would provide a response time of one hour or less.

Biosensor Distal Tips

Biosensor distal tips disclosed herein are able to detect and quantify analytes. "Detection" refers to determining whether or not an analyte is present. "Quantification" refers to determining how much of the analyte is present, or at what concentration it is present. Generally, sensors, including biosensors, have the ability to detect the presence of an analyte at lower concentrations than can be accurately quantified.

Biosensor distal tips disclosed herein have transducers to which one or more biocomponents comprising a dehalogenase, a hydrolase, a lyase and/or an oxygenase are immobilized, treated and/or stabilized. The biosensors may continuously monitor soil or an aqueous/liquid environment in situ to detect the presence and/or concentration of one or more analytes, such as s-triazines, chlorinated ethenes, orthosulfates, organophosphates, or amine-substituted chemicals. S-triazines include, for example, the chlorinated herbicide atrazine (used to control broadleaf and grassy weeds), simazine, terbuthylazine, propazine, cyanazine, deethylatrazine and deisopropylatrazine, plus other s-triazines, melamine, lindane and DDT. Chlorinated ethenes include, for example, tetrachloroethene (a.k.a., perchloroethene (PCE)), trichloroethene (TCE), dichloroethene isomers and vinyl chloride (VC). Organophosphates include, for example, the pesticides methyl parathion, chlorpyrifos, and diazinon; the nerve agent sarin; and solvents and plasticizers such as tributylphosphate, tris(2-ethylhexyl)phosphate and triphenyl phosphate. Organosulfates include, for example, cerebroside-3-sulfate, phenol sulfates, chondroitin sulfate, karatan sulfate, dermatan sulfate, choline sulfate, polysulfates of cellulose, heparitin sulfate, heparan sulfate, and heparin. Amine-substituted chemicals include, for example, melamine, ammeline, ammelide, serine, biotin, and aniline.

Techniques for detecting and measuring one or more analytes using ion-selective electrodes or optodes, which perform for example based on pH (hydrogen ion concentration or hydroxide ion concentration), ammonia concentration, peroxide concentration, and/or oxygen concentration are disclosed. In one aspect, a biosensor includes a fiber optic element (an optical fiber or bundle), the tip of which has a layer of bacteria atop a layer of a pH-sensitive fluorophore (dye). In another aspect, a biosensor includes a fiber optic element (an optical fiber or bundle), the top of which has a layer of bacteria atop a layer of an oxygen-sensitive fluorophore. In yet another aspect, the pH-sensitive biosensor and the oxygen-sensitive biosensor may be combined into a single biosensor. The bacteria may be selected such that they carry one or more enzymes to catalyze a reaction involving one or more analytes. For example, a single type of natural or recombinant bacteria may express more than one enzyme useful for detecting analytes. Alternatively, multiple types of bacteria, each expressing one enzyme useful for detecting a single analyte, may be combined on a biosensor distal tip. The enzymatic reaction(s) may, for example, release protons or hydroxide ions (and cause a detectable pH change), produce a measurable halide ion concentration, produce a measurable ammonia/ammonium ion concentration or consume oxygen. Further, prior to being 'glued' (immobilized or otherwise affixed) to the tip of the fiber optic transducer, the bacteria may be specially treated and/or stabilized.

The disclosed biosensors have distal tips which include an ion-sensing, an ammonia sensing, and/or an oxygen-sensing transducer for use in detecting one or more analytes and at least one biocomponent comprising a dehalogenase, a hydrolase, a lyase and/or an oxygenase. A dehalogenase may, for example, be selected from the hydrolases, subclass EC 3.8, or lyases, subclass EC 4.5 (TABLE 1A), for carrying out a dehalogenation of an analyte. An oxygenase may, for example, be selected from monooxygenases and dioxygenases selected from EC family 1.13 and EC family 1.14 (TABLE 2A), for carrying out an oxidation of an analyte. A hydrolase may, for example, be selected from subclass EC 3.1 (TABLE 3A), for carrying out a hydrolysis of an analyte. A hydrolase may, for example, be selected from subclass EC 3.5 (TABLE 3A), for carrying out a deamination of an analyte. A lyase may, for example, be selected from subclass EC 4.3 (TABLE 4A), for carrying out a deamination of an analyte. Advantages of the disclosed distal tips and biosensors include, without limitation:

Disposable use with real-time results. The distal tips and/or biosensors may be used for single or multiple use applications, or for continuous real-time monitoring over an extended period.

Simplicity and versatility. The distal tips and/or biosensors may be used to collect information about physical properties of a wide range of analytes without requiring sophisticated equipment and complicated procedures. Simplicity of design may reduce fabrication costs and allow for off-site use, thereby making information readily available.

Structural design. A combination of immobilization and stabilization provides a robust distal tip design.

Several biosensor tips having similar or dissimilar transducer types (e.g., optical, electrochemical) may be incorporated into a bundle providing a package of different types of information where the biosensors acquire information simultaneously or sequentially.

TABLE 1A

Exemplary dehalogenating enzymes for use in a biosensor. See "Enzyme Nomenclature" of the Nomenclature Committee of the International Union of Biochemistry and Molecular Biology (http://www.chem.qmul.ac.uk/iubmb/enzyme/) and from the University of MN Biocatalysis/Biodegradation Database (http://umbbd.ahc.umn.edu/).

| Enzyme name(s) | EC code | Known substrates (analytes) | Reference(s) |
| --- | --- | --- | --- |
| Enzyme subclass 3.8: hydrolases acting on halide bonds: | | | |
| alkyl-halide halidohydrolase(alkylhalidase, halogenase; haloalkane halidohydrolase; haloalkane dehalogenase) | 3.8.1.1 | Bromochloromethane | [1] |

TABLE 1A-continued

Exemplary dehalogenating enzymes for use in a biosensor. See "Enzyme Nomenclature" of the Nomenclature Committee of the International Union of Biochemistry and Molecular Biology (http://www.chem.qmul.ac.uk/iubmb/enzyme/) and from the University of MN Biocatalysis/Biodegradation Database (http://umbbd.ahc.umn.edu/).

| Enzyme name(s) | EC code | Known substrates (analytes) | Reference(s) |
|---|---|---|---|
| 2-haloacid halidohydrolase (2-haloacid dehalogenase, 2-haloalkanoid acid halidohydrolase; 2-haloalkanoic acid dehalogenase; L-2-haloacid dehalogenase; DL-2-haloacid dehalogenase) | 3.8.1.2 | Acts on 2-haloacids of short chain lengths, C2 to C4 | [2] [3] |
| haloacetate halidohydrolase (haloacetate dehalogenase, monohaloacetate dehalogenase) | 3.8.1.3 | Fluoroacetate and other haloacetates | [4] [5] |
| L-thyroxine iodohydrolase (reducing) (thyroxine deiodinase, thyroxine 5-deiodinase; diiodothyronine 5'-deiodinase; iodothyronine outer ring monodeiodinase; iodothyronine 5'-deiodinase) | 3.8.1.4 | A group of enzymes, removing iodine atoms sequentially from thyroxine. | [6] [7] [8] |
| 1-haloalkane halidohydrolase (haloalkane dehalogenase, 1-chlorohexane halidohydrolase; 1-haloalkane dehalogenase) | 3.8.1.5 | Acts on a wide range of 1-haloalkanes, haloalcohols, haloalkenes and some haloaromatic compounds. | [9] [10] [11] |
| 4-chlorobenzoate chlorohydrolase (4-chlorobenzoate dehalogenase, halobenzoate dehalogenase) | 3.8.1.6 | 4-chlorobenzoate and other halogenated benzoates | [12] [13] |
| 4-chlorobenzoyl CoA chlorohydrolase (4-chlorobenzoyl-CoA | 3.8.1.7 | Specific for dehalogenation at the 4-position. Can dehalogenate substrates bearing fluorine, chlorine, bromine and iodine in the dehalogenase) 4-position. This enzyme is part of the bacterial 2,4-dichlorobenzoate degradation pathway. | [14] [15] |
| atrazine chlorohydrolase | 3.8.1.8 | Atrazine, simazine, and other halogenated s-triazines | [16] [17] |
| s-triazine hydrolase | 3.8.1.— | | |
| dichloroacetate halidohydrolase | 3.8.1.— | | |
| DL-2-haloacid dehalogenase | 3.8.1.— | | |
| 1,3,4,6-tetrachloro-1,4-cyclohexadiene halidohydrolase | 3.8.1.— | | |
| cis-chloroacrylic acid dehalogenase | 3.8.1.— | | |
| trans-chloroacrylic acid dehalogenase | 3.8.1.— | | |

Enzyme subclass 4.5: lyases acting on carbon-halide bonds:

| Enzyme name(s) | EC code | Known substrates (analytes) | Reference(s) |
|---|---|---|---|
| DDT-dehydrochlorinase (DDT-ase) | 4.5.1.1 | DDT (1,1,1-trichloro-2,2-bis(4-chlorophenyl)ethane) | [18] [19] [20] |
| 3-chloro-D-alanine chloride-lyase (deaminating) (3-chloro-D-alanine dehydrochlorinase, B-chloro-D-alanine dehydrochlorinase) | 4.5.1.2 | 3-chloro-D-alanine | [21] [22] |
| dichloromethane chloride-lyase (chloride-hydrolysing) (dichloromethane dehalogenase) | 4.5.1.3 | Dichloromethane, dibromoethane, bromochloromethane, diiodomethane | [23] |
| L-2-amino-4-chloropent-4-enoate chloride-lyase (deaminating) (L-2-amino-4-chloropent-4-enoate dehydrochlorinase, L-2-amino-4-chloro-4-pentenoate dehalogenase) | 4.5.1.4 | L-2-amino-4-chloropent-4-enoate | [24] |

TABLE 1A-continued

Exemplary dehalogenating enzymes for use in a biosensor. See "Enzyme Nomenclature" of the Nomenclature Committee of the International Union of Biochemistry and Molecular Biology (http://www.chem.qmul.ac.uk/iubmb/enzyme/) and from the University of MN Biocatalysis/Biodegradation Database (http://umbbd.ahc.umn.edu/).

| Enzyme name(s) | EC code | Known substrates (analytes) | Reference(s) |
|---|---|---|---|
| 3-chloro-L-alanine chloride-lyase (adding thioglycolate) (S-carboxymethylcysteine synthase, S-carboxymethyl-L-cysteine synthase) | 4.5.1.5 | 3-chloro-L-alanine | [25] |
| halohydrin hydrogen-halide-lyase | 4.5.1.— | | |
| halohydrin hydrogen-halide-lyase B | 4.5.1.— | | |
| DDD dehydrochlorinase | 4.5.1.— | | |
| DDMS dehydrochlorinase | 4.5.1.— | | |
| gamma-hexachlorocyclohexane dehydrochlorinase 5-chloro-1,2,4-trihydroxybenzene dechlorinase | 4.5.1.— 4.5.1.— | | |
| tribromobisphenol lyase | 4.5.1.— | | |

TABLE 2A

Exemplary oxidizing enzymes for use in a biosensor.

| Enzyme name(s) | EC code | Known substrates (analytes) | Reference(s) |
|---|---|---|---|
| Enzyme subclass 1.13: monooxygenases acting on the CH—OH group of single donors with incorporation of molecular oxygen: | | | |
| catechol 1,2-dioxygenase | 1.13.11.1 | catechol, requires $Fe^{3+}$ | [26] |
| catechol 2,3-dioxygenase | 1.13.11.2 | catechol, requires $Fe^{2+}$ | [27] |
| protocatechuate 3,4-dioxygenase | 1.13.11.3 | 3,4-dihydroxybenzoate, requires $Fe^{3+}$ | [28] |
| gentisate 1,2-dioxygenase | 1.13.11.4 | 2,5-dihydroxybenzoate, requires $Fe^{2+}$ | [29] |
| homogentisate 1,2-dioxygenase | 1.13.11.5 | homogentisate, requires $Fe^{2+}$ | [30] |
| lactate 2-monooxygenase | 1.13.12.4 | (S)-lactate | [31] |
| Enzyme subclass 1.14: dioxygenases acting on the CH—OH group of paired donors with incorporation or reduction of molecular oxygen: | | | |
| toluene dioxygenase | 1.14.12.11 | toluene | [32] |
| naphthalene 1,2-dioxygenase | 1.14.12.12 | naphthalene | [33] |
| 2-chlorobenzoate 1,2-dioxygenase | 1.14.12.13 | 2-chlorobenzoate, requires $Fe^{2+}$ | [34] |
| salicylate 1-monooxygenase | 1.14.13.1 | salicylate | [35] |
| 4-hydroxybenzoate 3-monooxygenase | 1.14.13.2 | 4-hydroxybenzoate | [36] |
| phenol 2-monooxygenase | 1.14.13.7 | phenol, resorcinol and o-cresol | [37] |
| flavin-containing monooxygenase | 1.14.13.8 | N,N-dimethylaniline, as well as hydrazines, phosphines, boron-containing compounds, sulfides, selenides, iodide, as well as primary, secondary and tertiary amines | [38] |
| methane monooxygenase | 1.14.13.25 | methane, alkanes can be hydroxylated, alkenes are converted into epoxides; CO is oxidized to $CO_2$, ammonia is oxidized to hydroxylamine, and some aromatic compounds and cyclic alkanes can also be hydroxylated. | [39] |
| pentachlorophenol monooxygenase | 1.14.13.50 | pentachlorophenol, 2,3,5,6-tetrachlorophenol | [40] |
| alkane 1-monooxygenase | 1.14.15.3 | octane | [41] |

TABLE 3A

Exemplary hydrolyzing enzymes for use in a biosensor.

| Enzyme name(s) | EC code | Known substrates (analytes) | Reference(s) |
|---|---|---|---|
| Enzyme subclass 3.1: hydrolases acting on ester bonds: | | | |
| carboxylesterase | 3.1.1.1 | carboxylic esters | [42] |
| arylsulfatase | 3.1.6.1 | phenol sulfate | [43] |
| glycosulfatase | 3.1.6.3 | D-glucose 6-sulfate | [44] |
| N-acetylgalactosamine-6-sulfatase | 3.1.6.4 | chondroitin sulfate and keratan sulfate | [45] |
| choline-sulfatase | 3.1.6.6 | choline sulfate | [46] |
| cellulose-polysulfatase | 3.1.6.7 | polysulfates of cellulose and charonin | [47] |
| cerebroside-sulfatase | 3.1.6.8 | cerebroside 3-sulfate | [48] |
| N-acetylgalactosamine-4-sulfatase | 3.1.6.12 | N-acetyl-D-galactosamine 4-sulfate units of chondroitin sulfate and dermatan sulfate | [49] |
| iduronate-2-sulfatase | 3.1.6.13 | L-iduronate 2-sulfate units of dermatan sulfate, heparan sulfate and heparin | [50] |
| N-acetylglucosamine-6-sulfatase | 3.1.6.14 | N-acetyl-D-glucosamine 6-sulfate units of heparan sulfate and keratan sulfate | [51] |
| N-sulfoglucosamine-3-sulfatase | 3.1.6.15 | N-sulfo-D-glucosamine 3-O-sulfate units of heparin | [52] |
| monomethyl-sulfatase | 3.1.6.16 | monomethyl sulfate | [53] |
| glucuronate-2-sulfatase | 3.1.6.18 | 2-O-sulfo-D-glucuronate residues of chondroitin sulfate, heparin and heparitin sulfate | [54] |
| aryldialkylphosphatase (organophosphate hydrolase) | 3.1.8.1 | aryl dialkyl phosphates, organophosphorus compounds including esters of phosphonic and phosphinic acids | [55] |
| diisopropyl-fluorophosphatase (organophosphorus acid anhydrolase; organophosphate acid anhydrase) | 3.1.8.2 | diisopropyl fluorophosphate, acts on phosphorus anhydride bonds (such as phosphorus-halide and phosphorus-cyanide) in organophosphorus compounds | [56] |
| Enzyme subclass 3.5: hydrolases acting on carbon-nitrogen bonds, other than peptide bonds: | | | |
| melamine deaminase | | melamine | |
| asparaginase | 3.5.1.1 | L-asparagine | [57] |
| glutaminase | 3.5.1.2 | L-glutamine | [58] |
| ω-amidase | 3.5.1.3 | monoamide of a dicarboxylic | [59] |
| amidase | 3.5.1.4 | monocarboxylic acid amide | [60] |
| urease | 3.5.1.5 | urea | [61] |
| penicillin amidase | 3.5.1.11 | penicillin | [62] |
| biotinidase | 3.5.1.12 | biotin amide | [63] |
| nicotinamidase | 3.5.1.19 | nicotinimide | [64] |
| D-glutaminase | 3.5.1.35 | D-glutamine | [65] |
| barbiturase | 3.5.2.1 | barbiturate | [66] |
| allantoinase | 3.5.2.5 | allantoinase | [67] |
| β-lactamase | 3.5.2.6 | β-lactam | [68] |
| creatininase | 3.5.2.10 | creatine | [69] |
| cyanuric acid amidohydrolase | 3.5.2.15 | cyanuric acid | [70] |

TABLE 4A

Exemplary lyases for use in a biosensor.

| Enzyme name(s) | EC code | Known substrates (analytes) | Reference(s) |
|---|---|---|---|
| Enzyme subclass 4.3: lyases acting on carbon-nitrogen bonds: | | | |
| aspartate ammonia-lyase | 4.3.1.1 | L-aspartate | [71] |
| phenylalanine ammonia-lyase | 4.3.1.5 | L-phenylalanine | [72] |
| ethanolamine ammonia-lyase | 4.3.1.7 | ethanolamine | [73] |
| peptidylamidoglycolate lyase | 4.3.2.5 | peptidylamidoglycolate | [74] |
| 3-ketovalidoxylamine C—N— | 4.3.3.1 | 3-ketovalidoxylamine C—N-lyase | [75] |
| strictosidine synthase | 4.3.3.2 | 3-α(S)-strictosidine | [76] |
| deacetylisoipecoside synthase | 4.3.3.3 | deacetylisoipecoside | [77] |
| deacetylipecoside synthase | 4.3.3.4 | deacetylipecoside | [77] |

Features of the distal tip include: a biocomponent comprising at least one enzyme for carrying out a dehalogenation, oxidation, deamination or hydrolysis of an analyte; the biocomponent is immobilized to a surface of the tip; treatment of the biocomponent for maintaining a period of enzymatic efficacy; and the biocomponent stabilized by one or more of crosslinking a surface of the immobilized biocomponent, crosslinking a polymer layer to the biocomponent, adding a gel-hardening agent to the biocomponent, adding a stabilizing agent to the biocomponent, and modifying a component used to immobilize the biocomponent to the surface of the tip.

Detection of Halogenated Organic Compounds Using Dehalogenases

In an embodiment, a distal tip of a biosensor ion-sensing transducer for use in detecting an analyte comprising a halogenated organic compound is selected from the following: a pH optode, a pH electrode, a field-effect transistor (FET) and a halide ion-selective electrode (ISE). Analytes of interest include without limitation: s-triazine compounds, which include both pesticides and non-pesticides, such as atrazine, simazine, terbuthylazine, propazine, cyanarine, deethylatrazine and deisopropylatrazine, and others including those shown in FIG. 1 and listed in TABLE 5; beta-, or the more common, gamma-hexachlorocyclohexane ("lindane") and DDT (1,1,1-trichloro-2,2-bis(p-chlorophenyl)ethane). Microorganisms that can initiate pathways identified in TABLE 6 are for the widely used herbicide atrazine (degradation example shown in FIG. 2). Without limitation, these microorganisms include: *Pseudomonas* sp. ADP; *Ralstonia* sp. M91-3; *Clavibacter michiganese* sp. ATZ1; *Agrobacterium* sp. J14a; *Alcaligenes* sp. SG1; *Rhodococcus* spp. NI86/21, TE1; *Pseudomonas* spp. 192, 194; and *Streptomyces* sp. PS1/5.

S-triazines are characterized by a symmetrical hexameric ring consisting of alternating carbon and nitrogen atoms. Atrazine is one of the most commonly applied s-triazine herbicides (structure below):

TABLE 5

Non-pesticide s-triazine groups with comments about use and biodegradability.

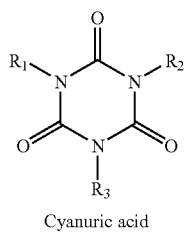
Cyanuric acid

Cyanuric (isocyanuric) acids: N-Chlorination of cyanuric acid at the R1, R2 and R3 sites yields chloroisocyanurates that are used as disinfectants (in swimming pools and hottubs), sanitizers (in household cleansers and automatic dishwashing compounds) and bleaches (in both the industrial and household bleaching of fabrics). The most common chloroisocyanurates are trichloro and dichloro isocyanuric acid (TCCA, DCCA) and sodium dichloroisocyanuric acid (SDCC).

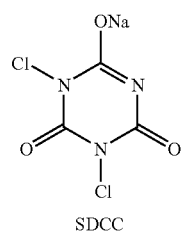
SDCC

Triallyl isocyanurate (R1, R2 and R3 = propenyl) is used as a crosslinking agent for poly(vinyl chloride) and other systems. Methylamine (also on the metapathway map) and N-substituted methylamines are sometimes used as finishing agents for textiles.

TABLE 5-continued

Non-pesticide s-triazine groups with comments about use and biodegradability.

RDX

Nitramine explosives: Cyclotrimethylenetrinitramine (RDX) is an explosive and a propellant used in military rockets. The partial biodegradation of RDX by mixed microbial culture is reported in (Binks et al. 1995).

Triazone

Triazone: A cyclic urea used as a crosslinking agent in textile finishing. 1,3-di-methylol-5-alkyltriazone is still widely used for this purpose. Crosslinking agents are used in the preparation of textiles to induce "memory" and to add luster.

Melamine

Melamine: A reagent in plastic manufacturing and a food contaminant that is illegally used to artificially increase protein content.

TABLE 6

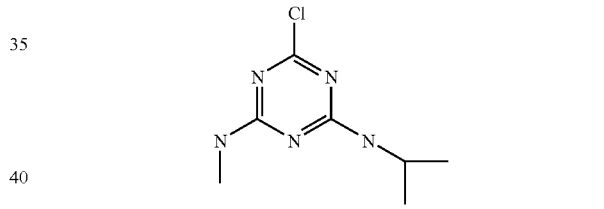

Atrazine degradation pathway map identifies organisms that can initiate the pathways shown.

| Atrazine | Atrazine | Atrazine |
|---|---|---|
| *Pseudomonas* sp. ADP | *Rhodococcus* spp. N186/21, TE1 | *Rhodococcus* spp. N186/21, TE1 |
| *Ralstona* sp. M91-3 | *Pseudomonas* spp. 192, 194 | *Pseudomonas* spp. 192,194 |
| *Calvibacter* sp. | *Streptomyces* sp. PS1/5 | *Streptomyces* sp. PS1/5 |
| *Agrobacterium* sp. J14a | atrazine monooxygenase | atrazine monooxygenase |
| *Alcaligenes* sp. SG1 | | |
| atrazine chloro-hydrolase | Deisopropylatrazine | Deethylatrazine |
| Hydroxyatrazine | *Rhodococcus corallinus* NRRLB-15444R | *Nocardia* sp. | *Pseudomonas* spp. 192, 194 |
| hydrozy-atrazine ethylamino-hydrolase | a-triazine hydrolase | deisopropyl-atrazine mono-oxygenase | deethyl-atrazine mono-oxygenase |

Figure 2:
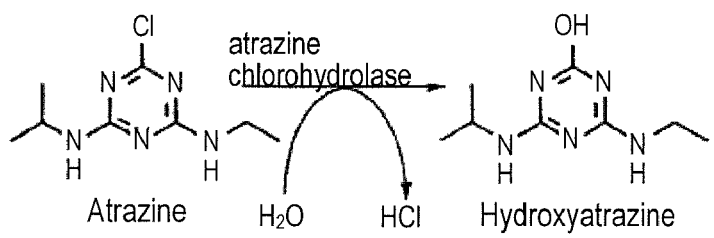
FIG. 2 depicts a hydrolytic dehalogenation of atrazine using atrazine chlorohydrolase.

FIG. 2 illustrates (see, also, left-hand column in above map) a hydrolytic dehalogenation of atrazine, the first step of which can be carried out by several microorganism species, such as *Pseudomonas* sp. ADP, *Ralstonia* sp. M91-3, *Clavibacter* sp. ATZ1, *Agrobacterium* sp. J14a and *Alcaligenes* sp. SG1. The reaction depicted in the middle column in the above map represents an oxygenase attack on the isopropyl amino group. This reaction can be carried out by several microorganism species, such as *Rhodococcus* spp. NI86/21 and TE1, *Pseudomonas* spp. 192 and 194, and *Streptomyces* sp. PS1/5. The reaction depicted in the right-hand column in the above map represents an oxygenase attack on the ethyl amino group. This reaction can be carried out by several species, such as *Rhodococcus* spp. NI86/21 and TE1, *Pseudomonas* spp. 192 and 194, and *Streptomyces* sp. PS1/5.

Two microorganisms suitable for use in degrading atrazine are *Pseudomonas* sp. strain ADP and *Clavibacter michiganese* ATZ1. Studies have shown that strain ADP has three genes (atz-A, atz-B and atz-C) that encode enzymes responsible for the degradation of atrazine to cyanuric acid. Strain ATZ1 has 100% homology only with atz-A; and thus only carries out reactions similar to the first two steps of strain ADP. For further reference, see TABLES 7.1-7.3 below:

TABLE 7.1

Physical methods used to design the ADP and ATZ1 biosensors

| | |
|---|---|
| PHYSICAL TRANSDUCER | Optical transduction: fluorescent dye |
| IMMOBILIZATION METHOD | Entrapment: Ca-alginate gel matrix, time of gelation = 20 minutes |
| BIOCOMPONENT | Whole cell of atrazine degrading strain: treated under various conditions |
| STABILIZATION METHOD | Storage in refrigerator at 4° C. |
| SIZE | Less than 2 mm diameter of immobilized gel: cell density ~1 g of wet wt. of cells/wt. of alginate |

TABLE 7.2

Summary of sensitivity parameters for the ADP and ATZ1 biosensors

| Microorganism used as a biocomponent | Linear Range (ppb) | Detection Limit | Response Time (90% of response for change of 25 ppb of atrazine conc., ~2 mm bead dia.) | Reproducibility (standard deviation based on 3 measurements) |
|---|---|---|---|---|
| ADP | 0-125 | <1 ppb | 19.7 ± 2.5 | <6% |
| ATZ1 | 0-100 | <1 ppb | 10.7 ± 2.3 | <5% |

TABLE 7.3

Summary of results of activity retention of the biosensors using different types of biocomponents.

| Type of microorganism Used as biocomponent | Activity retention >90% (days) | Activity retention >30% (days) |
|---|---|---|
| ADP | 5 | 7 |
| Heat-treated ADP | 7 (dry heating time = 30 sec) | 11 |
| | 9 (dry heating time = 60 sec) | 12 |
| Chloramphenicol- | 8 (Conc. of chloramphenicol = 50 μg/mL) | 9-10 |
| treated ADP | 10 (Conc. of chloramphenicol = 200 μg/mL) | 60% activity retention on the 12th day. |
| Protease inhibitor- treated ADP | 6 | 10 |
| ATZ1 | 5 | 11 |

Figure 3:
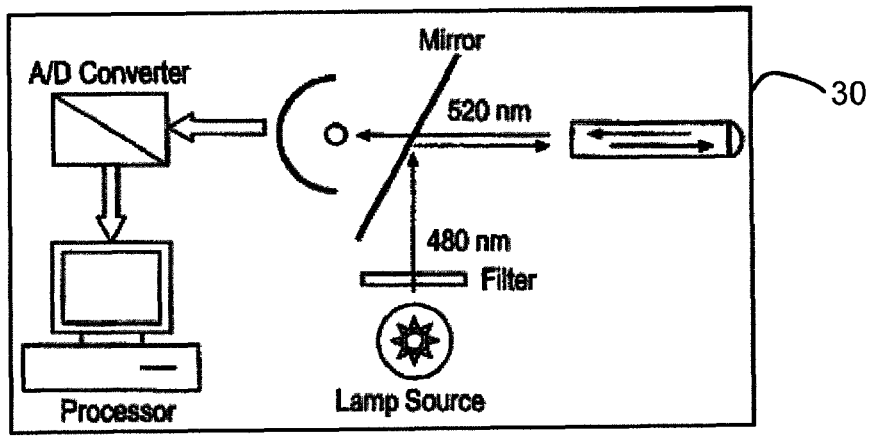
FIG. 3 schematically depicts features of a known system suitable for use in connection with a pH optode as the transducer (Campbell, 1998).

Once again, turning to the figures: FIG. 1 is a depiction of several pathways derived from general knowledge of the degradation of the s-triazine, atrazine. FIG. 2 depicts a hydrolytic dehalogenation of atrazine using atrazine chlorohydrolase. FIG. 3 schematically depicts features of a known system 30 suitable for use in connection with a pH optode as the transducer (Campbell, 1998). This fiber optic pH sensor system 30 includes the pH optode with biocomponent, a lens focusing system, a photomultiplier (PMT), an A/D converter and suitable microprocessor.

Figure 4:
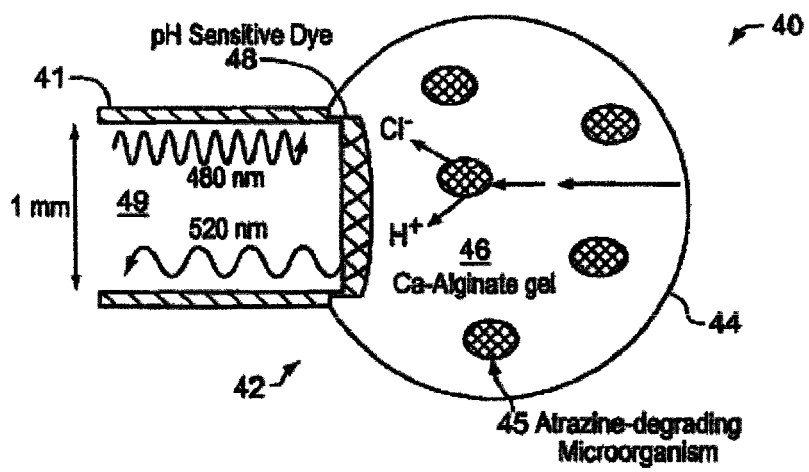
FIG. 4 schematically depicts features of a distal tip utilizing a pH optode to which a dehalogenase has been immobilized by entrapment within a hydrogel or polymer matrix, according to an embodiment.

FIG. 4 schematically depicts features of a distal tip 42, an embodiment utilizing a pH optode 49 to which biocomponent 44 comprising the dehalogenase 45 (either in pure form or carried in a microorganism at 45) has been immobilized by entrapment within a hydrogel or polymer matrix 46, shown enlarged for clarity. The pH optode 49 has suitable cladding 41 for purposes of protecting the fiber(s) of the optical element (single or bundle) therewithin. Information about the environment 40 (soil or aqueous, for example) can be collected as disclosed herein.

Figure 5:
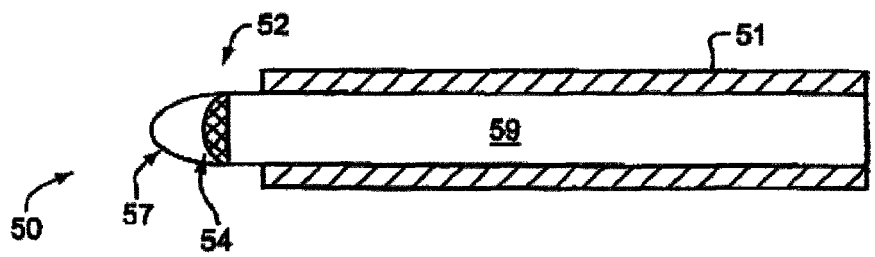
FIG. 5 schematically depicts features of a distal tip where two different matrices of a hydrogel or polymer are superimposed, and the layer adjacent the distal tip surface preferably has a higher concentration of dehalogenase than the outermost layer, according to an embodiment.

FIG. 5 schematically depicts features of a distal tip 52 where two different matrices of a hydrogel or polymer are superimposed, and the layer adjacent the distal tip 54 surface preferably has a higher concentration of dehalogenase (whether carried by whole cells or in purified form) than the outermost layer 57. The pH optode 59 has suitable cladding 51 for purposes of protecting the fiber(s) of the optical element (single or bundle) therewithin. Information about the environment 50 (soil or aqueous, for example) can be collected as disclosed herein.

Figure 6:
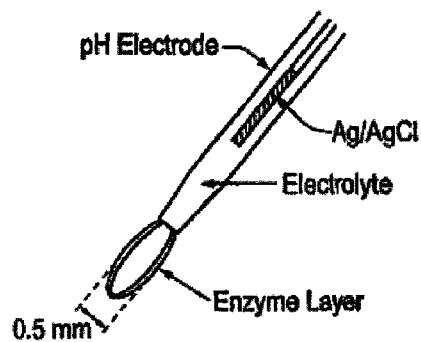
FIG. 6 schematically depicts features of a distal tip employing a pH microelectrode transducer, according to an embodiment.
Figure 7:
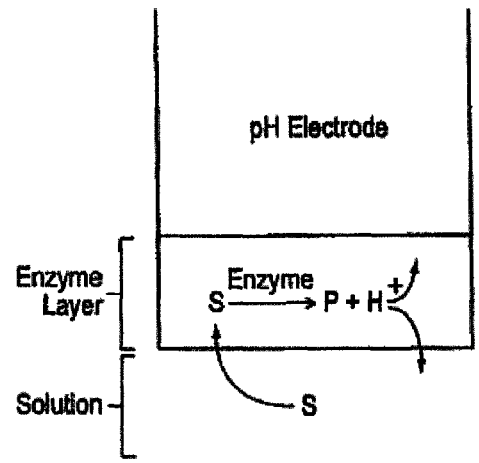
FIG. 7 schematically depicts further details of the pH electrode depicted in FIG. 6.
Figure 8:
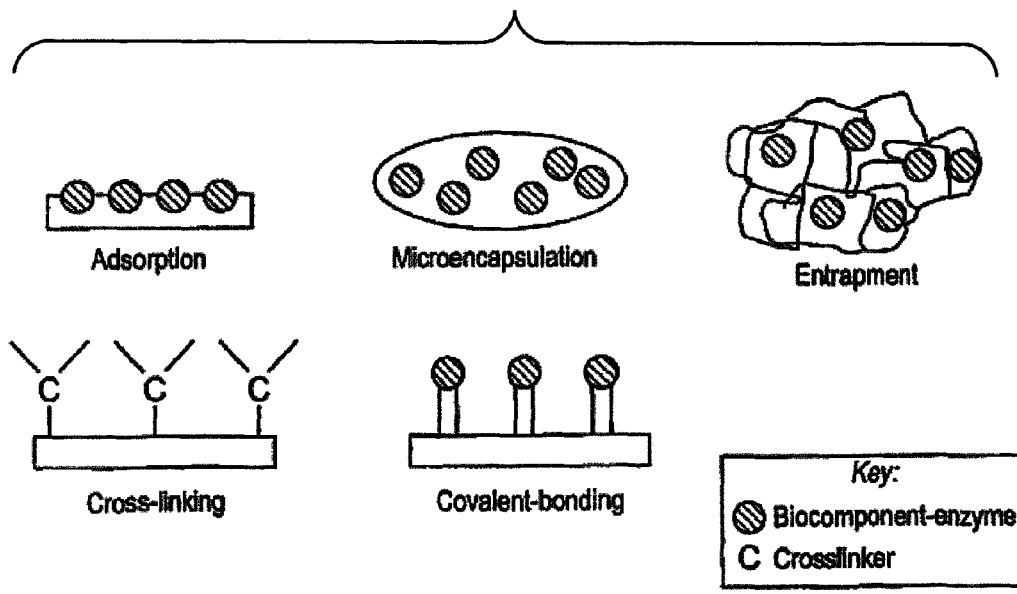
FIG. 8 schematically depicts several immobilization techniques, according to multiple embodiments.
Figure 9:
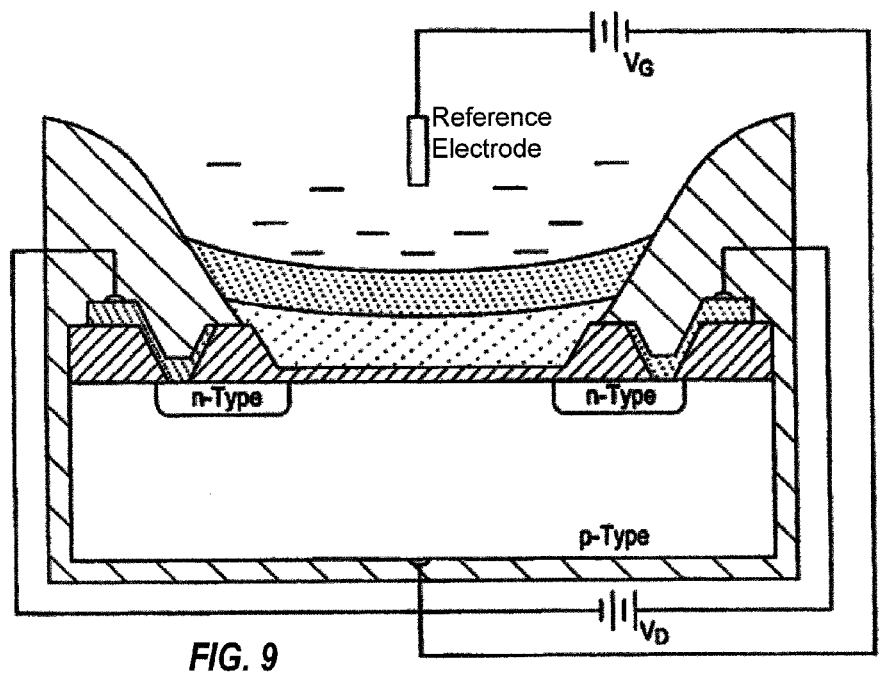
FIG. 9 schematically depicts features of a micro-sized biosensor where the transducer employed is a Field Effect Transistor (FET)-type to which a biocomponent is immobilized, according to an embodiment.
Figure 10:
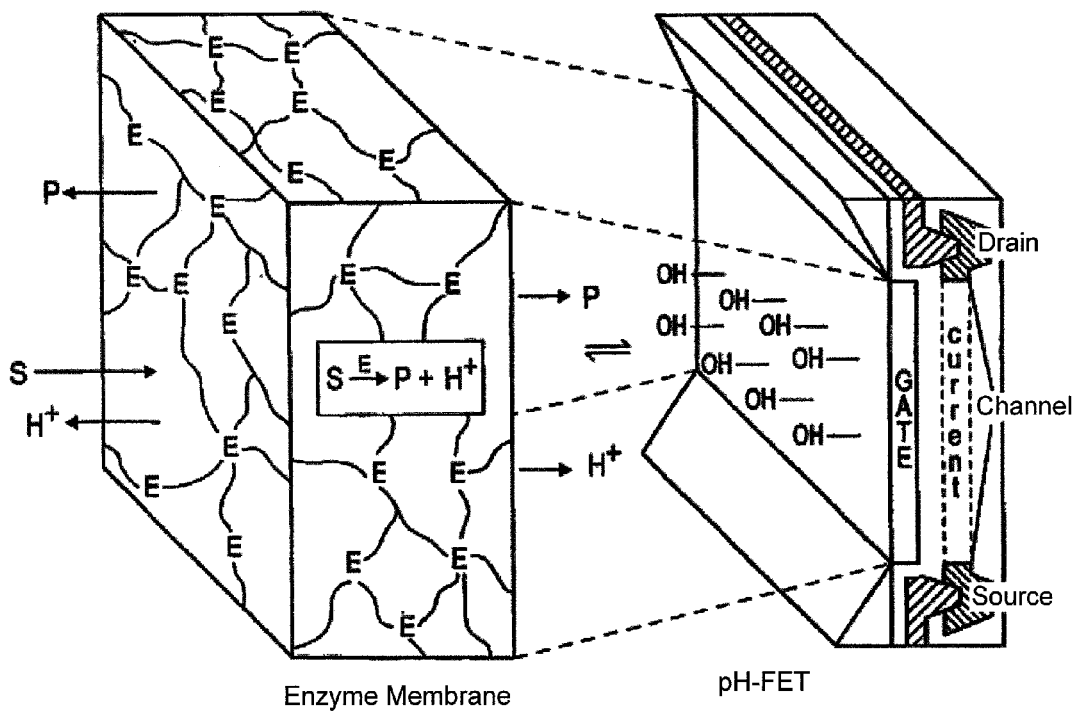
FIG. 10 schematically depicts further details of the pH-sensitive FET transducer depicted in FIG. 9.

FIG. 6 schematically depicts features of a distal tip embodiment employing a pH microelectrode transducer, an enzyme-containing biocomponent immobilized to the distal tip. FIG. 7 schematically represents further details of the pH electrode depicted in FIG. 6, featuring the reaction of the analyte (here, S, for 'substrate') within the enzymatic layer. In general terms, the diffusion of S results in products P and H⁺. FIG. 8 schematically represents several immobilization techniques as identified according to multiple embodiments. FIG. 9 schematically depicts features of a micro-sized embodiment where the transducer employed is a Field Effect Transistor (FET)-type to which a biocomponent is immobilized. FIG. 10 schematically represents further details of the pH-sensitive FET transducer depicted in FIG. 9, featuring the reaction of the analyte (here, S, for 'substrate') within the enzymatic layer.

One might choose to target a dehalogenase which produces a measurable pH change and needs no reactant other than the halogenated analyte (e.g., atrazine) and perhaps water. This methodology excludes the reductive dehalogenases, which require an ancillary reagent to be oxidized while the halogenated analyte is reduced, as well as other classes of enzymes that require oxygen or energy from the cell. On the other hand, methods of introducing oxygen and other reagents are described below, so enzymes requiring cofactors are not necessarily precluded from use as biocomponents in the present biosensors.

Detection of Organosulfate Compounds Using Hydrolases

In an embodiment, a distal tip of a biosensor ion-sensing transducer for use in detecting an analyte comprising an organosulfate organic compound is selected from the following: a pH optode, a pH electrode, a field-effect transistor (FET) and an ion-selective electrode (ISE). Analytes of interest include without limitation: cerebroside-3-sulfate, phenol sulfates, chondroitin sulfate, karatan sulfate, dermatan sulfate, choline sulfate, polysulfates of cellulose, heparitin sulfate, heparan sulfate, and heparin.

An ion-sensing biosensor may be based on the activity of sulfatase enzymes selected from subclass EC 3.1.6. Hydrolysis of an orthosulfate compound by a sulfatase produces protons that may, for example, be monitored using a pH-dependent biosensor having a fluorescent dye, such as carboxynaphthofluorescein. Alternatively, a chromophoric/fluorescent product, such as p-nitrophenol or coumarin, may be directly monitored by an optical detector.

Detection of Organophosphate Compounds Using Hydrolases

In an embodiment, a distal tip of a biosensor ion-sensing transducer for use in detecting an analyte comprising an organophosphate organic compound is selected from the following: a pH optode, a pH electrode, a field-effect transistor (FET) and an ion-selective electrode (ISE). Analytes of interest include without limitation: esters of phosphoric acid including pesticides, such as methyl parathion (O,O-dimethyl O-p-nitrophenyl phosphorothioate), parathion (O-p-nitrophenyl phosphorothioate), EPN (o-ethyl O-p-nitrophenyl phenylphosphonothioate), diazinone (O,O-diethyl O-2-isopropyl-4-methyl-6-pyrimidinylthiophosphate), malathion (S-1,2-bis(ethoxycarbonyl)ethyl O,O-dimethyl phosphorodithioate), paraoxon (diethyl 4-nitrophenyl phosphate), fenitrothion (O,O-dimethyl-O-(4-nitro-meta-tolyl)), coumaphos (O,O-diethyl O-(3-chloro-4-methyl-7-coumarinyl) phosphorothioate), diazinon (O,O-diethyl-O-(2-isopropyl-6-methyl-pyrimidine-4-yl)phosphorothioate) and chlorpyrifos (O,O-diethyl O-3,5,6-trichloro-2-pyridyl phosphorothioate), and nerve agents, such as Tabun, Sarin, Soman and VX.

An ion-sensing biosensor may be based on the activity of orthophosphorous hydrolase (OPH) enzymes selected from subclass EC 3.1.8.2 and/or organophosphorus acid anhydrolase (OPAA) enzymes selected from subclass EC 3.1.8.1 and/or carboxylesterase enzymes selected from subclass EC 3.1.1.1. Hydrolysis of an orthophosphate compound by OPH, OPAA or carboxylesterase produces protons that may, for example, be monitored using a pH-dependent biosensor having a fluorescent dye, such as carboxynaphthofluorescein. Alternatively, a chromophoric/fluorescent product, such as p-nitrophenol or coumarin, may be directly monitored by an optical detector. Similarly, enzyme catalyzed reaction products of parathion, methyl parathion, fenitrothion and EPN, such as p-nitrophenol (PNP), may be monitored amperometrically either directly or, for example, by conversion to hydroquinone, nitrocatechol or benezenetriol by oxygenases from PNP-degrading *Arthrobacter* species and *Moraxella* species.

Detection of Amine-Containing Compounds Using Hydrolases and Lyases

In an embodiment, a distal tip of a biosensor transducer for use in detecting an analyte comprising an amine-containing organic compound is selected from the following: an optical transducer, a pH optode, a pH electrode, a field-effect transistor (FET) and an ion-selective electrode (ISE). Analytes of interest include for example melamine, ammeline, ammelide, serine, biotin, and aniline.

A biosensor may be based on the activity of hydrolases selected from subclass EC 3.5 and/or lyases selected from subclass EC 4.3. From the subclass EC 3.5, suitable melamine deaminase enzymes are described, for example, in U.S. Pat. Nos. 5,508,193; 6,265,201; 6,284,522; 6,369,299 and 6,825,001. When the amine group alone is cleaved, it is released as ammonia ($NH_3$), which then reacts spontaneously with water, as shown in equation (1):

$$NH_3 + H_2O \Leftrightarrow NH_4OH \Leftrightarrow NH_4^+ + OH^- \qquad (1)$$

The production of $OH^-$ leads to an increase in pH, which may be detected by a pH electrode, an ion-selective electrode or a pH-dependent biosensor having a fluorescent dye, such as carboxynaphthofluorescein.

In the event that an amine-containing group is released in the cleavage reaction, a second enzyme—having specificity for the released product—can be employed to further cleave this product such that ammonia is released. Thus, two independent measurements of the same analyte may improve precision.

An array of biosensors based on deaminating enzymes could be constructed for the purposes of measuring the concentrations of amine-containing chemicals in mixtures, or to identify a specific amine-containing chemical, as discussed below.

Detection of Organic Compounds Using Oxygenases

In an embodiment, a distal tip of a biosensor oxygen-sensing transducer for use in detecting an analyte comprising an organic compound is an oxygen optode. More specifically, an optical enzymatic biosensor may be based on the activity of mono- and/or di-oxygenase enzymes selected from EC family 1.13 and EC family 1.14. These enzymes catalyze the reaction of oxygen with a wide range of organic chemicals, resulting in the consumption of molecular oxygen, as well as NADH or NADPH.

An oxygen-based biosensor typically contains a layer of oxygenase-expressing bacteria immobilized on the tip of an optical sensor. Since the reaction of oxygenase with analyte consumes molecular oxygen, the oxygen concentration at the tip of the optical fiber decreases, and the magnitude of the decrease is proportional to the concentration of analyte in the surrounding environment. An oxygen-sensitive fluorophore, such as tris(4,7-diphenyl-1,10-phenanthroline)ruthenium(II) chloride, may be immobilized on an optical fiber, e.g., a polymethylmethacrylate fiber. Alternatively, a commercially available FOXY fiber optic oxygen sensor (Ocean Optics Inc.) may be used. The optical fiber interfaces with an optical-electronic unit that provides excitation light of the correct wavelength for the oxygen-sensitive fluorophore (e.g., using a halogen lamp or light-emitting diode), and detects the emitted fluorescent light (e.g., using a photomultiplier tube).

Analytes of interest include without limitation: hydrocarbons found in petroleum-derived fuels such as benzene, toluene, xylene, and naphthalene, and chlorinated ethenes such as tetrachloroethene (a.k.a., perchloroethene (PCE)), trichloroethene, dichloroethene isomers and vinyl chloride (VC), which are the most frequently detected groundwater contaminants in the world. Biosensors described herein detect chlorinated ethenes at 0-100 μg/L (application-relevant levels).

Immobilization Techniques

Methods of producing a biosensor distal tip having an ion-sensing and/or oxygen-sensing transducer and at least one biocomponent for use in detecting one or more analytes are disclosed herein. An exemplary method includes: immobilizing the biocomponent(s) including at least one enzyme for carrying out a dehalogenation, a hydrolysis, a deamination and/or oxygenation of an analyte to a surface of the tip by one or more of (a) entrapping the enzyme within a hydrogel secured to the tip surface; (b) entrapping the enzyme within a polymeric network secured to the tip surface; (c) encapsulating the enzyme; (d) covalently bonding a second component of the biocomponent to the tip surface; (e) crosslinking the enzyme to a support material secured to the tip surface; and (f) adsorbing the enzyme into the tip surface; treating the biocomponent for maintaining a period of enzymatic efficacy; and stabilizing the biocomponent by one or more of crosslinking a polymer layer to the biocomponent, adding a gel-hardening agent to the biocomponent, adding a stabilizing agent to the biocomponent, and modifying a component used to immobilize the biocomponent to the surface of the tip.

The hydrogel or polymeric matrix used for entrapment of the biocomponent in the form of pure enzymes or whole cells (whether naturally occurring or recombinant) may be selected as follows: suitable hydrogels include algal polysaccharides (such as agar, agarose, alginate, and K-carrageenan), gelatin, collagen, pectin, poly(carbamoyl)sulfonate, locust bean gum and gellan; and suitable polymers include polyacrylamide, polystyrene, polymethacrylate, polyvinylalcohol and polyurethane. The biocomponent treatment may be selected from the following: applying an inhibitor of protein synthesis, adding a protease inhibitor, freeze drying and dry heating. Further focusing on particular features, the protein synthesis inhibitor may include any suitable antibiotic, such as one selected from chloramphenicol, aminoglycosides (e.g., kanamycin), tetracyclines and macrolides (e.g., erythromycin); the polymer layer crosslinked for stabilization may be selected from suitable polymers including poly-L-lysine (PLL), polyethylenimine, polyacrylic acid, polyvinyl alcohol, polyacrylamide and polyurethane; a crosslinking agent, such as glutaraldehyde, may be used to crosslink the biocomponent surface; and a suitable polyalcohol or sugar may be selected for addition to the biocomponent as a stabilizing agent.

It is critical that the biocomponent be properly bound to the transducer. Biocomponent immobilization techniques include:

Adsorption—Enzymes may be adsorbed onto, at least part of, one or more surfaces of a biocomponent material. Examples of materials to which enzymes may be adsorbed include: ion-exchange resins, ceramics, glass, polyvinyl chloride, chitin, chitosan, alumina, charcoal, glassy carbon, clay, cellulose, kaolin, silica gel and collagen. Adsorption has been classified as physical adsorption (physisorption) and chemical adsorption (chemisorption). Physisorption is usually weak and occurs via the formation of van der Waals bonds or hydrogen bonds between the substrate and the enzyme molecules. Chemisorption is stronger and involves the formation of covalent bonds.

Encapsulation—A thin microporous semipermeable membrane is used to surround the biocomponent. Because of the proximity between the biocomponent and transducer, and the minimal membrane thickness, biosensor response can be maximized. Suitable materials for encapsulation include, for example, nylon and cellulose nitrate. Further bonding of the biocomponent to the transducer surface may be accomplished using a conductive polymer, such as polypyrrole. The membrane may be selected for its ability to serve additional functions, such as selective ion permeability, enhanced electrochemical conductivity or mediation of electron transfer. Membrane types used for encapsulation include without limitation: cellulose acetate, polycarbonate, collagen, acrylate copolymers, poly(ethylene glycol), polytetrafluoroethylene (PTFE), agarose, as well as alginate-polylysine-alginate microcapsules formed of alginate and polylysine.

Entrapment—Cells or purified enzymes are physically constrained (entrapped) inside a three-dimensional matrix. Suitable materials (both natural and synthetic) for entrapment include those that permit substantially uniform cell distribution and have biocompatibility and good transport mechanisms. Such materials include without limitation alginate, agarose and collagen. One might also choose to utilize mild polymerization techniques for more rugged immobilization. Hydrogels are preferably used as agents for biosensor entrapment. They provide a hydrophilic environment for the biocomponent and require only mild conditions to polymerize. Hydrogels can absorb large quantities of water, which can facilitate desirable reactions such as hydrolysis. Both natural and synthetic hydrogels are suitable for use. The naturally occurring algal polysaccharides, such as agar, agarose, alginate and carrageenan, and synthetic polymers, such as polyacrylamide, polystyrene and polyurethane, are examples of suitable hydrogels. Synthetic polymers generally have a smaller pore size which can lead to less leakage of biocomponent, and hence longer stability; however, synthetics are generally toxic and the immobilization process is accompanied by generation of heat and production of free radicals. Natural polymers are typically non-toxic and biodegradable, and the immobilization process is less stressful to the biocomponent. Natural polymers may, however, provide less mechanical strength and stability, and their larger pore size may allow for predation by protozoans and other soil or water dwelling predators, as well as degradation by hydrolase enzymes within the environment being tested.

Alginate, a hydrogel formed via a gentle encapsulation process, provides a good, biocompatible microenvironment for a biocomponent. Alginate is a naturally occurring linear polymer composed of $\beta$-(1,4) linked D-mannuronic acid and $\alpha$-(1,4)-L-guluronic acid monomers. Commercially, alginate is obtained from kelp, but bacteria such as *Azotobacter vinelandii*, several *Pseudomonas* species and various algae also produce alginate. When alginate is exposed to $Ca^{+2}$ ions, a crosslinking network is formed by the bonding of $Ca^{+2}$ ions and polyguluronic portions of the polymer strand by a process known as ionic gelation. The gelation process is temperature-independent. Complete gelling time without cells may be as little as 30 minutes. Sol gel technology has enabled extension of the entrapment principle to silicate networks that have some advantageous characteristics, such as requiring milder polymerization processes and matrices that exhibit good mass transport and molecular access properties, particularly for electrochemical and optical transduction modes.

Crosslinking—The biocomponent is chemically bonded to a solid support or supporting material, such as a gel. Bifunctional agents such as glutaraldehyde, hexamethylene diisocyanate and 1,5-dinitro-2,4-difluorobenzene may be used to bind the biocomponent to the support. By way of example, a tyrosinase biosensor for polyphenols was made by pretreating the electrode via polymerization of pyrrole in 0.1 M tetraethylammonium sulfonate on the surface of the biosensor. The tyrosinase solution and glutaraldehyde were then repetitively and alternately coated on the surface to crosslink the enzyme to the polypyrrole surface. While there is little leaching of the biocomponent and the layer tends to exhibit long-term stability under strenuous experimental conditions, such as exposure to flowing samples, stirring, washing, etc., crosslinking causes damage to enzymes and may limit diffusion of analyte during operation.

Covalent Bonding—A particular chemical group present in the biocomponent, which is not involved in catalytic action, may be attached to a support matrix (transducer or membrane) by covalent bonding. Radicals that take part in such a reaction are generally nucleophilic in nature (e.g., —$NH_2$, —COOH, —OH, —SH and imidazole groups). In order to retain enzyme activity, the reaction is typically performed under mild conditions. Materials suitable for covalent bonding include without limitation: cellulose and cellulose derivatives, silica, glass, dextran, starch, agarose, porous silica, chitin and chitosan.

Transduction Techniques

The nature of the interaction of the biocomponent with the analyte impacts the choice of transduction technology. Transduction techniques can be categorized as follows:

Amperometric electrode (an electrochemical transducer)—A constant potential is maintained on a working electrode with respect to a reference electrode, and the current generated by oxidation or reduction of an electroactive species at the surface of the working electrode is measured; the response is linear. The reference electrode need not be drift-free to have a stable response. Since the signal generated is highly dependent on mass transfer of the electroactive species to the electrode surface, there can be a loss in sensitivity due to fouling by species that adsorb to the electrode surface. Enzymes, particularly oxidoreductases, are well suited to amperometric transduction as their catalytic activity is concerned with electron transfer. Electroactive species that can be monitored at the electrode surface include substrates of a biological reaction (e.g., $O_2$, NADH), final products (e.g., hydrogen peroxide for oxidase reactions, benzoquinone for phenol oxidation) and also electrochemical mediators that can directly transfer electrons from an enzyme to a working electrode surface (e.g., hexacyanoferrate, ferrocene, methylene blue).

Potentiometric electrode (an electrochemical transducer)—The potential difference between an active electrode and a reference electrode is measured under zero current flow. The three most commonly used potentiometric devices are ion-selective electrodes (ISEs), gas-sensing electrodes and field-effect transistors (FETs). All of these devices obey a logarithmic relationship between the potential difference and the activity of the ion of interest. Thus, potentiometric electrode sensors have a wide dynamic range. One disadvantage of potentiometric electrodes is the requirement of an extremely stable reference electrode. ISEs are commonly used to monitor aqueous environments (groundwater, waste water, etc.). FETs are commercially attractive because they can be used to build micro-biosensors according to currently available, widely used micro-electronic device production techniques.

Conductimetric electrode (an electrochemical transducer)—Conductimetric electrodes are used to measure salinity of marine environments. Conductance is measured by the application of an alternating current between two noble-metal electrodes immersed in a solution. Due to specific enzyme reactions, the electrodes convert neutral substrates into charged products, causing a change in conductance.

Optical Transducers—Several types of photometric behavior are utilized by optical biosensors: ultraviolet-visible absorption, fluorescence (and phosphorescence) emission, bioluminescence, chemiluminescence, internal reflection spectroscopy (evanescent wave technology) and laser light scattering methods. When fluorescent reagents are utilized, a fluorescent substance is excited by incident light and, as a result, the substance emits light of a longer wavelength. The intensity of emitted light changes as analyte binds with the fluorescent substance. The change in intensity can be measured as a response to a particular analyte. Suitable fluorescent reagents include trisodium 8-hydroxy-1,3,6-trisulphonate for pH sensors, fluoro(8-anilino-1-naphthalene sulphonate) for $Na^+$ ion sensors, and acridinium- and quinidinium-based reagents for halides. Chemiluminescence occurs by the oxidation of certain substances, usually with oxygen or hydrogen peroxide, to produce visible light. Bioluminescence is produced by certain biological substances, such as luciferins produced by firefly. Internal reflectance is a method based on the principle of total internal reflection of a light beam into an optically dense medium when the incident angle is greater than the critical angle. When such a process occurs, not all of the energy is confined in the optically dense medium. The internally reflected light generates an electromagnetic evanescent wave, which penetrates the lower density medium at the point of reflection, for a distance comparable to the wavelength of light. Techniques falling within the category of "light scattering" include: quasi-elastic light-scattering spectroscopy, photon correlation spectroscopy and laser Doppler velocimetry.

Stabilization of an Immobilized Biocomponent

The active lifetime of a biosensor, i.e., its period of enzymatic efficacy, depends upon the type of biocomponent used. Sensor lifetime can vary from a few days to a few months. Generally, pure enzymes have the lowest stability, while cell and tissue preparations provide longer lifetimes. There are three aspects of lifetime of a biosensor: the active lifetime of the biosensor in use, the lifetime of biosensor in storage, and the lifetime of the biocomponent in storage prior to being immobilized.

Stabilization of an immobilized biocomponent is important in order to maximize performance of the biosensor, especially where a biosensor is to be stored for a prolonged period of time before use. Stabilization techniques depend on the biocomponent and type of transducer employed. Techniques for stabilizing a biocomponent include:

Molecular Modification—The stability of enzymes can be improved by changing certain amino acids in the protein sequence, such as by site-directed mutagenesis, grafting of polysaccharides (or short chains of sugar molecules) onto the protein molecules, and other methods involving chemical and carbohydrate modifications.

Crosslinking, Covalent Bonding, Entrapment, Encapsulation—These techniques, considered useful as immobilization methods, can be used as supplements to the immobilization technique. The techniques improve enzyme stability by, for example: reducing the protein's mobility and thereby reducing degradation of its three-dimensional structure or preventing loss of biocomponent from the immobilization matrix. For example, a selected gel-hardening agent, such as glutaraldehyde, polyethyleneimine, hexamethylenediamine or formaldehyde, may be used as a stabilizing agent in connection with entrapment as the mode of immobilization.

Freeze Drying (Lyophilization)—Freeze drying can provide for long-term preservation of microorganisms and enzymes. It involves removal of water from frozen bacterial suspensions by sublimation under reduced pressure. This process is performed in the presence of cryoprotective agents, such as glycerol and DMSO, which reduce damage caused during freezing. Dried cells can be kept for a long period at 4° C. if oxygen, moisture and light are excluded. The cells can later be rehydrated and restored to their previous state. Two types of useful freeze drying include centrifugal freeze drying and pre-freezing. Microorganisms that are sensitive to freeze drying can be dried using the liquid-drying method.

Heat Shock—A heat shock process involves heating vacuum-dried cells at a high temperature (~300° C.) for a very short time (~2-3 minutes). With the proper temperature and heating time selected for cell type, cells can be killed but retain a viable enzyme system. These dead cells can be kept for a long time away from moisture without any requirement of nutrients.

Addition of Carbohydrates and Polymers—Freeze-dried enzymes are often stabilized by the addition of stabilizers, such as polyalcohols and sugars like trehalose, maltose, lactose, sucrose, glucose and galactose. This stabilization is due to the interaction of the polyhydroxyl compound with water in the system, which effectively reduces interaction between protein and water, thereby strengthening hydrophobic interactions of the protein molecule to its surroundings.

Freezing—The metabolic activities of a microorganism may be reduced by storing the microorganism at very low temperatures (−150° C. to −190° C.) using liquid nitrogen.

Oxygenases as Biosensor Detection Elements

A biosensor utilizing monooxygenase enzymes and/or dioxygenase enzymes as the biocomponent may be used to detect oxygen-consumption in a biosensor environment. Oxygenase enzymes use molecular oxygen and insert either one atom (monooxygenases) or two atoms (dioxygenases) into an organic substrate. For example, cells containing oxygenase enzymes, which catalyze an oxygen-consuming reaction, may be layered on the tip of a fiber optic sensor (an oxygen optode), to form an optical biosensor.

Using whole cells, the final products of monooxygenase attack on chlorinated ethenes are chloride and carbon dioxide:

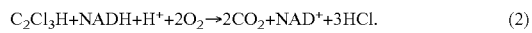  (2)

Hence, for whole cells, TCE is converted to $CO_2$ and chloride ions through formation of TCE epoxide. Other chlorinated ethenes (e.g., cis-DCE, trans-DCE and VC) have also been shown to degrade in a similar manner through epoxides under the action of monooxygenases. Although chlorinated epoxides are toxic to the bacteria that produce them, this toxicity has been substantially reduced by cloning genes for glutathione-S-transferase and glutathione synthesis (Rui, L., Y.-M. Kwon, K. F. Reardon, and T. K. Wood, "Metabolic Pathway Engineering to Enhance Aerobic Degradation of Chlorinated Ethenes and to Reduce Their Toxicity by Cloning a Novel Glutathione S-Transferase, an Evolved Toluene o-Monooxygenase, and γ-Glutamylcysteine Synthetase," *Environmental Microbiology*, 2004, 6: pp. 491-500). In addition, toxicity has been reduced by using DNA shuffling and site-directed mutagenesis to create epoxide hydrolase enzymes from *Agrobacterium radiobacter* AD1 which detoxify the chloroepoxides (Rui, L. Y., L. Cao, W. Chen, K. F. Reardon, and T. K. Wood, "Active site engineering of the epoxide hydrolase from *Agrobacterium* radiobacter AD1 to enhance aerobic mineralization of cis-1,2-dichloroethylene in cells expressing an evolved toluene ortho-monooxygenase," *Journal of Biological Chemistry*, 2004. 279 (45): pp. 46810-46817).

It was previously thought that PCE was completely resistant to oxygenase attack; however, it has been shown that the fully chlorinated PCE may be degraded by aerobic systems using toluene/xylene-o-monooxygenase (ToMO) from *P. stutzeri* (Ryoo, D., H. Shim, K. Canada, P. Barbieri, and T. K. Wood, "Aerobic Degradation of Tetrachloroethylene by Toluene-o-Xylene Monooxygenase of *Pseudomonas stutzeri* OX1," *Nature Biotechnology*, 2000. 18 (7): pp. 775-778). It has also been discovered that the chlorinated aliphatics PCE, TCE, 1,1-DCE, cis-DCE, trans-DCE, VC and chloroform may all be degraded individually and as mixtures by ToMO (Shim, H., D. Ryoo, P. Barbieri, and T. K. Wood, "Aerobic Degradation of Mixtures of Tetrachloroethylene, Trichloroethylene, Dichloroethylenes, and Vinyl Chloride by Toluene-o-Xylene Monooxygenase of *Pseudomonas stutzeri* OX1," Applied Microbiology and Biotechnology, 2001. 56: pp. 265-269; Chauhan, S., P. Barbieri, and T. K. Wood, "Oxidation of Trichloroethylene, 1,1-Dichloroethylene, and Chloroform by Toluene/o-Xylene Monooxygenase from *Pseudomonas stutzeri* OX1," *Applied and Environmental Microbiology*, 1998. 64 (8): pp. 3023-3024). In the case of TCE and PCE, nonspecific oxygenases have been found that allow co-metabolic degradation of chlorinated species (Arciero, D.; T. Vannelli, M. Logan, and A. B. Hooper, "Degradation of Trichloroethylene by the Ammonia-Oxidizing Bacterium, *Nitrosomonas europaea*," *Biochemistry and Biophysics Research Communications*, 1989. 159: pp. 640-643; Little, C. D., A. V. Palumbo, S. E. Herbes, M. E. Lidstrom, R. L. Tyndall, and P. J. Gilmer, "Trichloroethylene Biodegradation by a Methane-Oxidizing Bacterium," *Applied and Environmental Microbiology*, 1988. 54 (4): pp. 951-956; Shim, 2001).

As shown in equation (1), conversion of TCE requires input of NADH and $O_2$. This requirement for cofactors is common to all of the chlorinated ethenes, and has limited the development of biosensors utilizing oxygenases. The present inventors have developed methods, described below, to address delivery of cofactors.

Oxygen Delivery

Figure 11:
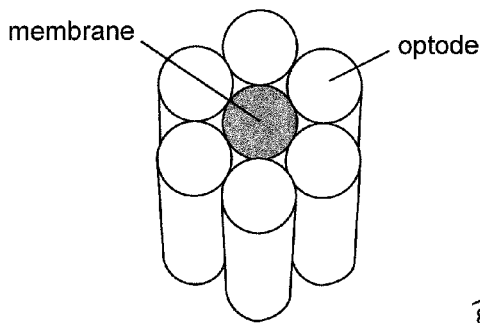
FIG. 11 schematically depicts a fiber optic biosensor array having a capillary tube charged with a reagent, such as oxygen or hydrogen peroxide, according to an embodiment.

Oxygen may be delivered through microcapillary tubing, to overcome sensor dependence on the local dissolved $O_2$ concentration. FIG. 11 schematically depicts a fiber optic biosensor array having a capillary tube charged with one to two bars of oxygen. The capillary tube may, for example, have a diameter of about 1 to 2 mm (600 to 1600 µm ID). One end of the capillary may be fused shut, while the other end—the end proximal to the biosensor distal tips—may be capped with an oxygen permeable membrane. Such membranes are ubiquitous in the gas separation industry (Noble, R. D. and S. A. Stern, eds. *Membrane Separations Technology: Principles and Applications*. 1995, Elsevier. 499-552). Selecting a membrane with low permeation flux ($<10^{-7}$ mol cm$^{-2}$ s$^{-1}$) should ensure that $O_2$ remains in a saturated state in the liquid phase near the membrane surface without reaching a supersaturated state such that bubbles form. For the low mass transfer rates required to supply oxygenases with sufficient oxygen, it may be possible to use dense inorganic membranes (van der Haar, L. M. and H. Verweij, "Homogeneous porous perovskite supports for thin dense oxygen separation membranes," Journal of Membrane Science, 2000. 180: pp. 147-155) having intrinsic permeation fluxes up to three orders of magnitude lower than typical polymeric membranes. It is known that oxygen diffusing through a membrane will quickly saturate the liquid near the surface—less than 0.005 seconds is needed to saturate the liquid within 10 µm of the membrane surface (Seinfeld, J. H. and S. N. Pandis, Atmospheric Chemistry and Physics: From Air Pollution to Climate Change. 1998, New York: John Wiley & Sons), and Henry's law can be used to calculate the liquid phase $O_2$ concentration at the interface. The saturated dissolved $O_2$ concentration at the membrane surface will drive diffusive mass transfer of oxygen away from the surface. In some embodiments, a ratio of oxygen capillaries to biosensors may be between 6:1 to 1:50, or between 1:1 to 1:25, or between 1:6 to 1:10. To optimize use of $O_2$ by the oxygenases, the oxygen capillary may be ringed by four to ten fiber optical biosensors, depending on capillary diameter, as shown in FIG. 11. In an embodiment; this bundle of fiber optic cables surrounding an oxygen capillary may be viewed as a base unit, so that if more biosensors are required the unit can be repeated as necessary. It will be appreciated that the base unit may include cladding.

Calculations have been made to demonstrate the feasibility of the base unit configuration. In the model, a 1 mm diameter membrane is ringed by six 1 mm diameter optodes. Water surrounding the membrane and optodes is initially free of dissolved $O_2$, and oxygen diffuses away from the membrane into pure water. The monooxygenase reactions are not included in this model, so the predicted diffusion rates will be lower than in the actual system. For the temperature used in the model, 298 K, the saturated $O_2$ concentration at the membrane surface will be $1.3 \times 10^{-3}$ M, with 1 bar $O_2$ in the capillary.

Figure 12:
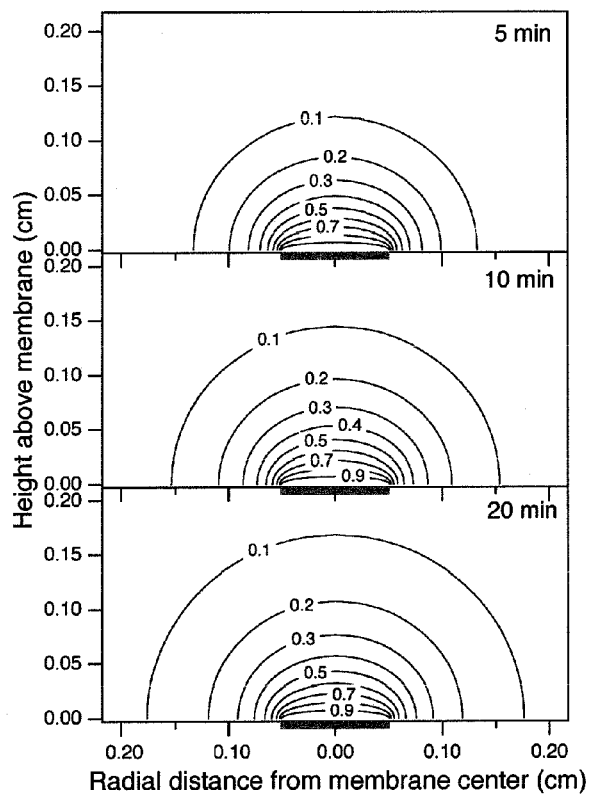
FIG. 12 depicts contours representing a fraction of maximum dissolved $O_2$ concentration, $1.3 \times 10^{-3}$ M, in an aqueous solution above an oxygen-filled capillary.

The contours in FIG. 12 indicate fractions of this saturated concentration at three different times. After only five minutes of operation, the minimum dissolved $O_2$ concentration above the 1 mm optodes is $10^{-4}$ M, a value three times greater than the level at which oxygen limits the rate of oxygenase reactions (Leahy, J. G. and R. H. Olsen, "Kinetics of toluene degradation by toluene-oxidizing bacteria as a function of oxygen concentration, and the effect of nitrate," *FEMS Microbiology Ecology*, 1997. 23 (1): pp. 23-30). Further, for the conditions considered, the calculated $O_2$ dissolution rates indicate that a 600 μm ID, 10 cm long capillary will contain enough oxygen for more than two weeks of biosensor operation. This two week figure is lower bound because the dissolution rate will be slower if the aqueous sample contains any dissolved $O_2$ when the experiment begins.

Alternatively, an oxygen capillary may have a distal end that is attached to a continuous and replaceable oxygen source, rather than a fused end that encloses a fixed concentration of oxygen.

Hardware for Fiber Optic Monitoring of Single Contaminants

Fiber optic biosensors suffer from less signal loss than electronic sensors, so they can be used at longer distances, and they have a small size, typically 1 mm or less in diameter, that allows them to be easily transported and utilized in a wide range of applications. The small size of fiber optic sensors allows for bundling of sensors for different contaminants into an optical cable that provides simultaneous measurements with one device. Fiber optic sensors also allow for low cost, simultaneous measurements at different locations or depths (i.e., spatial resolution), as well as continuous monitoring (i.e., temporal resolution).

Fiber optic oxygen sensors (oxygen "optodes") as transducers for enzyme biosensors have been described (Wolfbeis, O. S., *Fiber Optic Chemical Sensors and Biosensors, Vols. I and II*. 1991, Boca Raton: CRC Press; Scheper, T., C. Müller, K. D. Anders, E. F., F. Plotz, O. Thordsen, and K. Schügerl, "Optical Sensors for Biotechnological Applications," *Biosens. Bioelectron.*, 1994. 9 (1): pp. 73-83). These sensors are based on attenuation by oxygen of the fluorescence of a tip-immobilized dye, which is often a ruthenium complex (Amao, Y., "Probes and polymers for optical sensing of oxygen," *Microchimica Acta*, 2003. 143 (1): pp. 1-12; Tang, Y, T. E. C., Tao Z Y, Bright F V, "Sol-gel-derived sensor materials that yield linear calibration plots, high sensitivity, and long-term stability," *Analytical Chemistry*, 2003. 75 (10): pp. 2407-2413; Zhang P, Guo J, Wang Y, Pang W, "Incorporation of luminescent tris(bipyridine)ruthenium(II) complex in mesoporous silica spheres and their spectroscopic and oxygen-sensing properties," *Materials Letters*, 2002. 53 (6): pp. 400-405; Klimant, I. and O. S. Wolfbeis, "Oxygen-Sensitive Luminescent Materials Based on Silicone-Soluble Ruthenium Diimine Complexes," *Analytical Chemistry*, 1995. 67 (18): pp. 3160-3166).

Higher $pO_2$ levels at the optode will quench the florescence of the dye on the oxygen optode tip; thus, the dynamic response of these biosensors to an analyte will be opposite that of the pH-based biosensors. Namely, oxygen-based biosensors fluoresce more as oxygen is consumed whereas pH-based biosensors fluoresce more as protons are produced. Measurement of the $pO_2$-dependent florescence requires an optoelectronic instrumentation system to provide optical excitation to the optode, collect florescence, and convert this optical signal into an amplified electronic signal with minimal noise. In addition to maximum sensitivity, application to in situ groundwater contamination monitoring requires the optoelectronic instrumentation to be portable with corresponding constraints on size, weight, ruggedness and power consumption. Similar hardware has previously been developed for pH-based fiber optic biosensors (see FIG. 3).

An exemplary system comprises an optical excitation source, a fiber optic system for delivering the excitation and returning the florescence signal, a photodetector for optical to electronic conversion, and electronic amplification and signal processing circuitry. Although halogen lamps have previously been used for florescence excitation in fiber optic florescent sensors, advances in blue and ultraviolet GaN LED technology over the past decade have made LEDs a superior choice due to their better fiber coupled power efficiency, adequate spectral characteristics without filtering, easy modulation at MHz rates and long operating life. GaN laser diodes or near-infrared laser diodes doubled into the blue with non-linear optic crystals may also be used. The fiber optic system must separate the return florescence out of the same fiber used to carry the excitation to the optode. Options for splitting include bifurcated fibers, double-clad fibers, multimode fiber couplers, fiber or free-space dichroic beam splitters and circulators. The optical geometry of the fiber optic probe is also important, and improvements have been reported with the use of tapered fibers (Fielding, A. J. and C. C. Davis, "Tapered Single-Mode Optical Fiber Evanescent Coupling," *IEEE Photonics Technology Letters*, 2002. 14 (1): pp. 53-55). Photomultiplier tubes (PMTs) and avalanche photodiodes (APDs) offer internal electrical gain and are often used for high sensitivity florescent detection. However, cost, weight, size and power supply requirements favor simpler hybrid p-i-n photodiodes with integrated amplifiers and may offer sufficiently low noise for many applications.

Researchers have developed oxygen-based sensors for ethanol (Mitsubayashi, K., T. Kon, and Y. Hashimoto, "Optical bio-sniffer for ethanol vapor using an oxygen-sensitive optical fiber," *Biosensors & Bioelectronics*, 2003. 19 (3): pp. 193-198), glucose (Wolfbeis, O. S., I. Oehme, N. Papkovskaya, and I. Klimant, "Sol-gel based glucose biosensors employing optical oxygen transducers, and a method for compensating for variable oxygen background," *Biosensors and Bioelectronics*, 2000. 15 (1-2): pp. 69-76), L-glutamate (Dremel, B. A. A., R. D. Schmid, and Wolfbeis O, S., "Comparison of 2 fiber-optic L-glutamate biosensors based on the detection of oxygen or carbon-dioxide, and their application in combination with flow-injection analysis to the determination of glutamate," *Analytica Chimica Acta*, 1991. 248 (2): pp. 351-359), lactate, cholesterol and other analytes. However, development of enzymatic biosensors has been limited where NADH is required as a cofactor.

The Peroxide Shunt

Although NADH-requiring biosensors have been made (Lisdat, F. and U. Wollenberger, "Trienzyme amplification system for the detection of catechol and catecholamines using internal co-substrate regeneration," *Analytical Letters*, 1998. 31 (8): pp. 1275-1285), their long-term use and performance are limited because of problems encountered in supplying NADH. Thus, any oxygenase sensor must either provide an alternative electron donor or recycle NADH (Park, D. H., C. Vieille, and J. G. Zeikus, "Bioelectrocatalysts—Engineered oxidoreductase system for utilization of fumarate reductase in chemical synthesis, detection, and fuel cells," *Applied Biochemistry and Biotechnology*, 2003. 111 (1): pp. 41-53). In electronic biosensors, efforts have been made to directly supply electrons. However, this approach has limitations, requiring very stable enzymes that nonetheless do not survive long on the biosensor surface.

Figure 13:
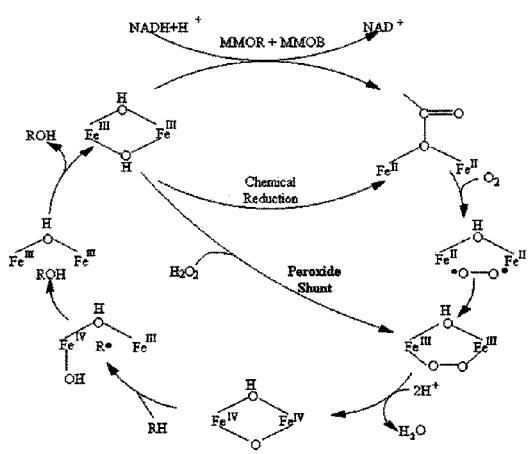
FIG. 13 schematically depicts the monooxygenase peroxide shunt pathway.

An alternative approach to addressing the "NADH problem" is to utilize the so-called peroxide shunt (see FIG. 13). This approach has not been implemented in biosensors, but it is known that hydrogen peroxide can be used, instead of NADH, to donate both two electrons and atomic oxygen in the monooxygenase reaction (Jiang, Y., P. C. Wilkens, and H. Dalton, "Activation of the Hydroxylase of sMMO from *Methylococcus capsulatus* (Bath) by Hydrogen Peroxide," *Biochimica et Biophysica Acta*, 1993. 1163: pp. 105-112). With the peroxide shunt, $O_2$ and NADH are no longer needed for monooxygenase-catalyzed oxidations. This mechanism has been shown for methane monooxygenases and toluene o-monooxygenase (Newman, L. M. and L. P. Wackett, "Purification and Characterization of Toluene 2-Monooxygenase from *Burkholderia cepacia* G4," *Biochemistry*, 1995. 34: pp. 14066-14076), which along with the entire family of TCE-degrading monooxygenases contains a common oxygen-bridged iron cluster, Fe—O—Fe, in the common 250 KDa hydroxylase.

The peroxide shunt may remove the need for NADH regeneration, which may increase biosensor lifetime since living cells are not required, where electrons and oxygen are supplied in the form of peroxide, and energy metabolism is no longer necessary. This is important for some oxygenases, such as those that act on chlorinated aliphatics, since these enzymes are not stable outside the cell (Fox, B. G., W. A. Froland, J. E. Dege, and J. D. Lipscomb, "Methane Monooxygenase from *Methylosinus trichosporium* OB3b," *Journal of Biological Chemistry*, 1989. 264 (17): pp. 10023-10033; Oppenheim, S. F., J. M. Studts, B. G. Fox, and J. S. Dordick, "Aromatic hydroxylation catalyzed by toluene-4-monooxygenase in organic solvent/aqueous buffer mixtures," *Applied Biochemistry & Biotechnology*, 2001. 90: pp. 187-197).

The peroxide shunt changes the overall reaction of TCE, from that shown in equation (2), to:

$$C_2Cl_3H + H_2O_2 \rightarrow 2CO_2 + 3HCl. \quad (3)$$

Based on equation (3), at least three detection schemes are feasible: detection of pH changes using fluoresceinamine fluorescence (higher TCE concentrations result in lower pH values); co-immobilization of catalase and iron or $MnO_2$ to catalyze the breakdown of $H_2O_2$ to $O_2$ and $H_2O$, and detection of $O_2$ (higher TCE concentrations result in lower $O_2$ concentrations); detection of $H_2O_2$ removal using luminol chemiluminescence.

The first approach is similar to that described above to produce biosensors based on dehalogenases. $H_2O_2$ sensors based on the second and third options have been reported (Freeman, T. M. and W. R. Seitz, "Chemiluminescence fiber optic probe for hydrogen peroxide based on the luminol reaction," *Anal. Chem.*, 1978. 50: pp. 1242-1246; Genovesi, L., H. Pedersen, and G. H. Sigel. *The development of a generic peroxide sensor with application to the detection of glucose*. in SPIE—International Society of Optical Engineering. 1988), as have glucose biosensors based on the third approach (Swindlehurst, C. A. and T. A. Nieman, "Flow-injection determination of sugars with immobilized enzyme reactors and chemiluminescence detection," *Anal. Chim. Acta*, 1988. 205: pp. 195-205).

A key requirement of being able to use the peroxide shunt is delivery of $H_2O_2$ to the cells on the optical fibers. The peroxide concentration must be high enough to drive the reaction, but low enough so as not to damage the cells or impact the environment of the sensor tip. Delivery of $H_2O_2$ may occur via diffusion from a membrane-capped capillary tube that may be bundled with the optical fibers, in a manner analogous to the delivery of oxygen described above (FIG. 11).

Biosensor Arrays for Evaluating Mixtures of Analytes

In biosensor arrays, where a number of different biocomponents are present, each providing a signal, the set of signals may be interpreted to provide multianalyte identification and measurement. With effective chemometric analysis to interpret the signal set, sensor arrays have been shown to be highly effective at resolving analyte mixtures, even if each individual sensor is only moderately specific and the analyte range of one sensor overlaps with that of another (Epstein, J. R. and D. R. Walt, "Fluorescence-based fibre optic arrays: a universal platform for sensing," Chemical Society Reviews, 2003. 32 (4): pp. 203-214; Schauer, C. L. F. J. Steemers, and D. R. Walt, "A cross-reactive, class-selective enzymatic array assay," *Journal of the American Chemical Society*, 2001. 123 (38): pp. 9443-9444; Albert, K. J., N. S. Lewis, C. L. Schauer, G. A. Sotzing, S. E. Stitzel, T. P. Vaid, and D. R. Walt, "Cross-reactive chemical sensor arrays," *Chemical Reviews*, 2000. 100 (7): pp. 2595-2626; Lee, M. and D. R. Walt, "A fiber-optic microarray biosensor using aptamers as receptors," *Analytical Biochemistry*, 2000. 282 (1): pp. 142-146).

To evaluate mixtures of analytes, an array of biosensors can be employed, where each biosensor utilizes a different biocomponent or a mixture of biocomponents (and each biocomponent interacts with one type of fluorophore on the biosensor that fluoresces at a particular wavelength). In an embodiment, individual biocomponents may detect analytes that are not chemically similar. For example, one biocomponent on a biosensor in an array may detect a halogenated organic compound, while another biocomponent on the same or a different biosensor in the array detects a heavy metal, and a third biocomponent on the same or a different biosensor in the array detects starch.

In another embodiment, biosensors/biocomponents in an array may detect closely-related, chemically similar compounds. In this case, a single type of biocomponent, e.g., toluene o-monooxygenase (TOM), may detect multiple analytes, e.g., TCE and DCE. In order to detect and resolve closely-related compounds, each biosensor in an array may utilize a different variant of one type of biocomponent. The biocomponent variants have different specificities for each analyte, which allows for measurement and resolution of complex mixtures.

To illustrate how the use of variant biocomponents addresses the detection and quantification of similar analytes in a mixture, the following example is provided. Consider three biosensors, each of which responds linearly to increasing concentrations of each of three similar analytes. If the response factors of the biosensor/analyte pairs are those shown in TABLE 8 (response factor=sensor signal/analyte concentration), the response of each of the sensors to a mixture of the three analytes can be described by the algebraic equations:

$$S_1 = 10C_A + 5C_B + 1.5C_C$$

$$S_2 = 3C_A + 8C_B + 1.5C_C$$

$$S_3 = 1.5C_A + 3C_B + 7C_C$$

in which $S_i$ is the signal of each sensor (1, 2 or 3) and $C_j$ is the concentration of the analyte (A, B or C). When a single sensor is placed in a sample of unknown concentrations $C_A$, $C_B$ and $C_C$, the resulting signal (e.g., $S_1$) cannot be used to determine the individual values of $C_A$, $C_B$ and $C_C$. However, if all three $S_i$ values are available, then the equations above can be solved to yield the values $C_A$, $C_B$ and $C_C$.

TABLE 8

Hypothetical linear response factors of three sensors to three analytes when each analyte is measured separately from the others.

| Response factor for: | Analyte A | Analyte B | Analyte C |
|---|---|---|---|
| Sensor 1 | 10 | 5 | 1.5 |
| Sensor 2 | 3 | 8 | 1.5 |
| Sensor 3 | 1.5 | 3 | 7 |

In more complex situations, the response of a biosensor to an analyte may not be linear. Methods from the field of chemometrics, the application of statistics to chemical problems, can be applied to the information obtained by biosensor arrays. For example, principle component analysis is well suited for linear problems, while neural networks can be used for nonlinear problems. Although the minimum number of biosensors/biocomponents in an array must be equal to the number of analytes to be detected, it will generally be desirable to have more biosensors/biocomponents present in an array to provide redundant information and thus more certainty in the resulting measurements.

Transducers for biosensor arrays include any of those described above which utilize any optical, electrochemical or physical method that allows the signal from each biosensor in the array to be measured independently.

Biocomponents with different ranges of specificity can be developed or obtained through a variety of methods, including bioprospecting, DNA shuffling and/or selection by display (e.g., yeast or phage), as described in more detail below.

DNA Shuffling/Saturation Mutagenesis

Frequently, known enzymes do not have certain desired properties (e.g., selectivity toward TCE). Although traditional mutagenesis methods can be used to improve enzymes, they are slow and not likely to truly optimize the enzyme. Directed evolution or DNA shuffling (Stemmer, W. P. C., "DNA Shuffling by Random Fragmentation and Reassembly: In vitro Recombination for Molecular Evolution," *Proceedings of the National Academy of Sciences*, 1994. 91: pp. 10747-10751; Stemmer, W. P. C., "Rapid Evolution of a Protein in vitro by DNA Shuffling," *Nature*, 1994. 370: pp. 389-391; Crameri, A. and W. P. C. Stemmer, "Combinatorial Multiple Cassette Mutagenesis Creates All the Permutations of Mutant and Wild-Type Sequences," *BioTechniques*, 1995. 18 (2): pp. 194-196; Crameri, A., E. A. Whitehorn, E. Tate, and W. P. C. Stemmer, "Improved Green Fluorescent Protein by Molecular Evolution Using DNA Shuffling," *Nature Biotechnology*, 1996. 14: p. 315-319) is a powerful mutagenesis technique that mimics the natural molecular evolution of genes in order to efficiently redesign them. The power of DNA shuffling lies in its ability to introduce multiple mutations into a gene in order to create new enzymatic activity.

DNA shuffling uses PCR without oligo primers to reassemble a gene from random 10-300 bp DNA fragments generated by first cleaving the gene with DNase. After reassembling the original gene from these fragments using a series of homologous recombinations and extensions with dNTPs and polymerase, normal PCR is performed to yield the full-length gene with random mutations. The mutations arise from infidelity in the assembly process, PCR infidelity and errors introduced in the assembly process by insertion of mutated gene fragments (controlled by the researcher by adding specific oligos or DNA fragments from related but not identical genes). DNA shuffling advantageously introduces mutations much more efficiently than other methods, and it may be used to create a chimeric gene by reassembling closely related genes. It has been used to increase β-lactamase antibiotic activity by 32,000-fold (Stemmer, *Nature*, 1994), to increase the fluorescence of green fluorescent protein by 45-fold (Crameri, 1996), and to evolve a fucosidase from β-galactosidase (Zhang, J.-H., G. Dawes, and W. P. C. Stemmer, "Directed Evolution of a Fucosidase from a Galactosidase by DNA Shuffling and Screening," *Proceedings of the National Academy of Sciences*, 1997. 94: pp. 4504-4509). In the presently disclosed biosensors, DNA shuffling may be used, for example, to increase the specificity of monooxygenases for chlorinated ethenes.

Molecular breeding, the combination of similar genes from different bacteria to introduce even greater genetic diversity (Minshull, J. and W. P. C. Stemmer, "Protein Evolution by Molecular Breeding," *Current Opinion in Chemical Biology*, 1999. 3: pp. 284-290), may also be used with a set of monooxygenase genes to make advances in enzymatic activity for chlorinated ethenes. Molecular breeding has been used successfully to produce better subtilisin proteases by combining twenty-six unrelated protease genes (Ness, J. E., M. Welch, L. Giver, M. Bueno, J. R. Cherry, T. V. Borchert, W. P. C. Stemmer, and J. Minshull, "DNA Shuffling of Subgenomic Sequences of Subtilisin," *Nature Biotechnology*, 1999. 17: pp. 893-896).

Saturation mutagenesis may also be used to enhance enzyme selectivity since it can be used to introduce all possible mutations at key sites, for activity identified by DNA shuffling, or adjacent sites to explore a larger fraction of the protein sequence space. Saturation mutagenesis can provide more comprehensive information than can be achieved by single-amino acid substitutions and can overcome drawbacks of random mutagenesis.

Hardware for Monitoring Multiple Optodes

Oxygen optode hardware based on fiber optic sensors is readily adaptable to the collection of measurements from multiple sensors. Each of the multiple optical biosensors may be connected to an optoelectronic instrumentation system, described above, via its own dedicated fiber. In an embodiment, optical source and detection hardware can be used to interrogate a number of fiber sensors by switching connections. A biosensor array system may use commercially available fiber optic switches to allow a single optical source and detector to be switched between the different fiber probes on a time scale of milliseconds with minimal insertion loss. However, low cost LED and amplified p-i-n technology may be used to obtain adequate sensitivity, and separate sources and detectors may instead be provided for each channel, thereby creating a system that can provide tradeoffs between redundancy for greater reliability and the number of different channels.

Example 1

A biosensor employing a pH optode with dehalogenase carried by whole cells immobilized by gel entrapment as a biocomponent was produced by the following method (see FIGS. 5 and 7). A distal tip was coupled to a 1 m long polymethylmethacrylate (PMMA) fiber optic cable. Cells stored at 4° C. in phosphate-buffered saline were centrifuged at 15,000×g for 2 minutes. The pellet was washed twice with saline (9 g/L NaCl, pH 7.1) containing 50 µg/mL of chloramphenicol. Next, sodium-alginate (4% w/v in water) containing about 100 µg/mL of chloramphenicol was added and mixed well with the cell pellet. This cell-alginate mixture was kept for 5 minutes at room temperature before it was used to make the biosensor. The cell-alginate mixture was stirred well with a pipette tip and a small drop of the gel was carefully deposited on the tip of the pH optode. The tip was dipped into an ice-cold solution of 7% (w/v) of $CaCl_2.2H_2O$ for 15 minutes to form a crosslinked network. After immobilization, the tip was about 2 mm in diameter. A protease inhibitor cocktail in 1 mL of saline solution was prepared by adding 215 mg of lyophilized protease inhibitor in a solution containing 1 mL DMSO (dimethyl sulfoxide) and 4 mL deionized water. The cocktail had a broad specificity for the inhibition of serine, cysteine, aspartic and metalloproteases, and aminopeptidases.

Example 2

A biosensor was prepared with microorganism strain ADP encapsulated in alginate, according to the method of Example 1, and then coated with poly-L-lysine (PLL). The Ca-alginate bead on the biosensor tip (nearly 1 mm) was washed twice with saline solution (9 g/L NaCl in water). The biosensor tip was immersed in 10 mL of 0.4% (w/v) of poly-L-lysine followed by HCl in saline for 30 minutes at 30° C. In order to remove unreacted PLL from the bead surface, the tip was washed with saline solution.

Example 3

Figure 14:
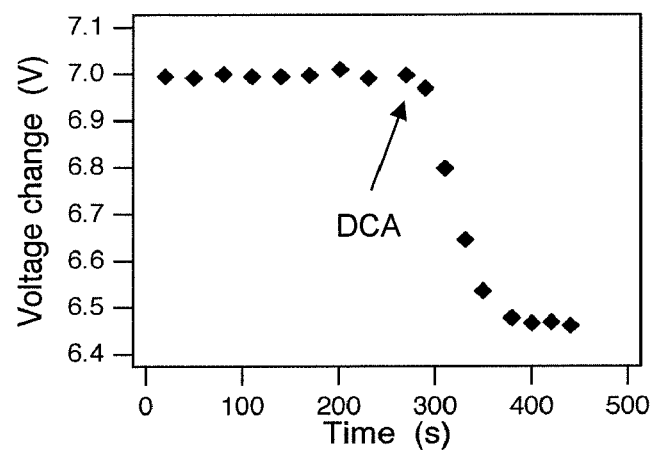
FIG. 14 depicts a time course of biosensor response to 4.7 ppb of 1,2-dichloroethane using *X. autotrophicus* GJ10 DhlA dehalogenase as the biocomponent, according to an embodiment.
Figure 15:
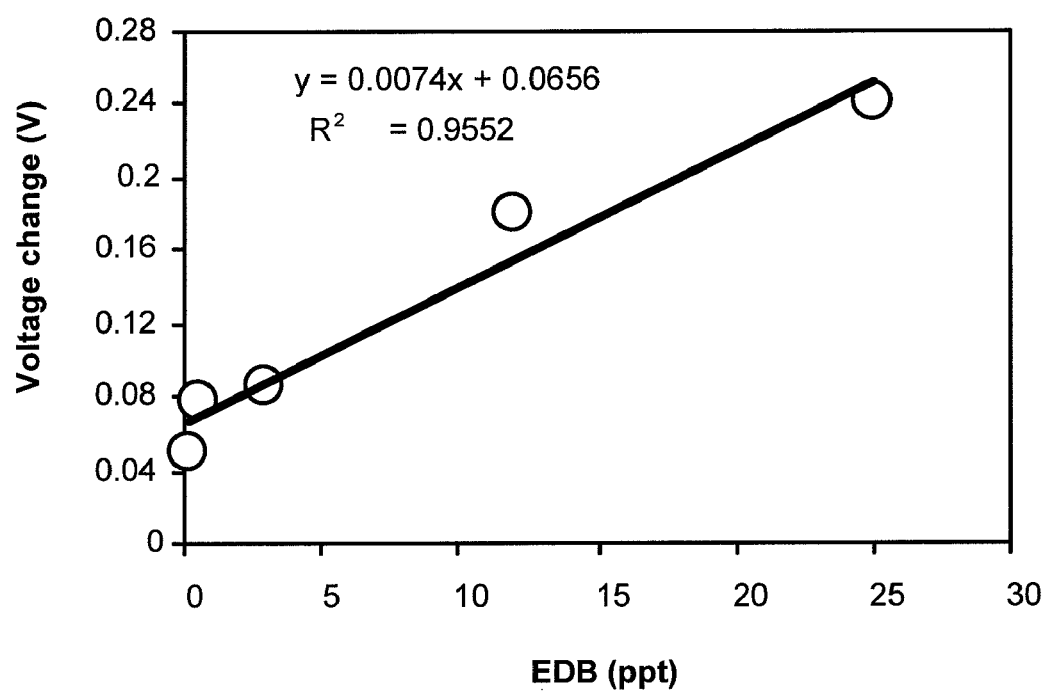
FIG. 15 depicts a calibration curve for an ethylene dibromide (EDB) biosensor, according to an embodiment.
Figure 16:
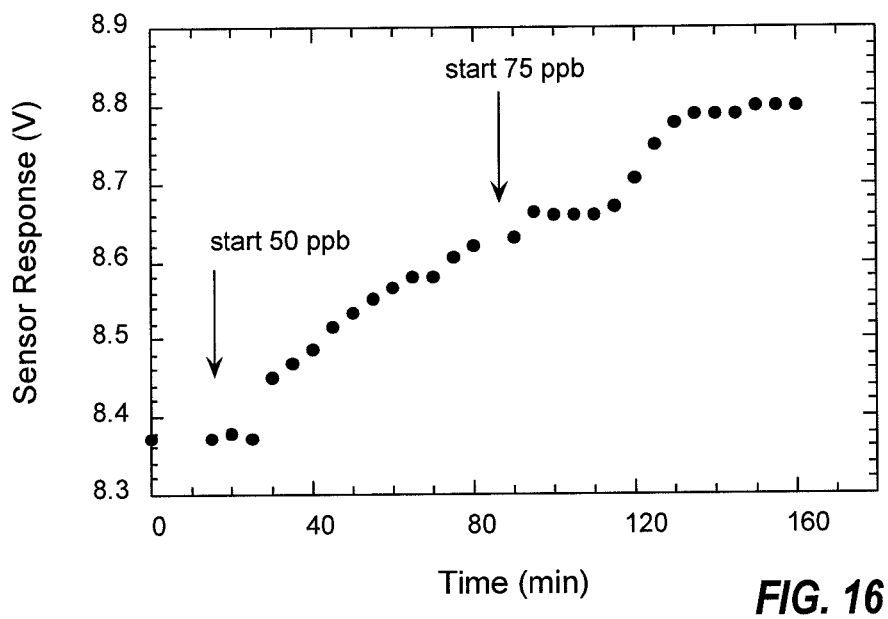
FIG. 16 depicts results of atrazine monitoring in a soil column, according to an embodiment.

The release of a proton from the dehalogenation reaction is detected as a pH change at the end of the optical fiber, and thus as a change in fluorescence intensity (FIG. 14). Fiber optic biosensors for 1,2-dichloroethane (DCA), ethylene dibromide (EDB), atrazine, 1-chlorohexane and Lindane (γ-hexachlorocyclohexane) have been developed (Campbell, 1998; Das, N., *Development and Characterization of a Biosensor for Atrazine in Groundwater*, Chemical Engineering. 2000, Colorado State University: Fort Collins). These biosensors have linear response ranges over several orders of magnitude in concentration, and detection in the ppt (ng/L) range has been achieved (FIG. 15). Because dehalogenases do not require energy or cofactors, the cells in which they are immobilized need not be living. This fact, and the stability of the enzymes, allows the biosensors to retain activity for many weeks. In one test (FIG. 16), the biosensor response to 5 ppb of 1,2-dibromoethane declined by only 20% in more than 50 days. Sensitive measurement is still possible even at the end of the test; only a recalibration is required.

Example 4

Figure 17:
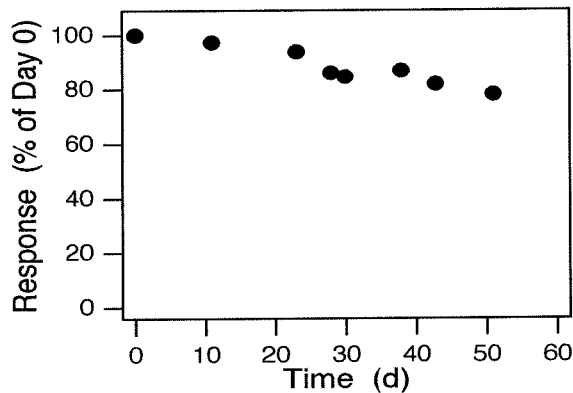
FIG. 17 depicts a biosensor response to 5 μg/L 1,2-dibromoethane using *E. coli* pAQN (linB) as the biocomponent, measured repeatedly over 50 days, according to an embodiment.

The ability of the biosensors to provide a continuous signal and to function in a soil environment has been demonstrated in laboratory soil column tests. Atrazine at three increasing concentrations was pumped through a 0.5 m glass column filled with silty sand and the signal from an atrazine biosensor was monitored (FIG. 17). Responses are scaled to Day 0.

Example 5

Figure 18:
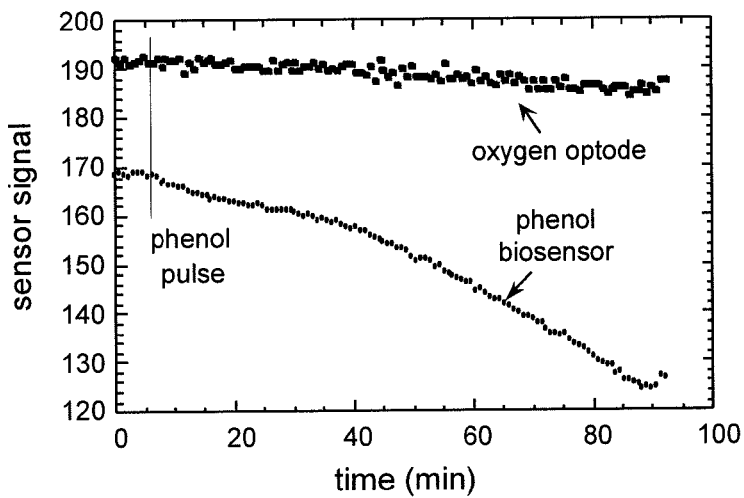
FIG. 18 depicts results from phenol monitoring using *Burkholderia cepacia* JS150, immobilized in calcium alginate on the end of an oxygen optode, as the biocomponent, according to an embodiment.

FIG. 18 shows the response of a biosensor to a pulse of phenol. The biocomponent was *Burkholderia cepacia* JS150, immobilized in calcium alginate on the end of an oxygen optode. Initially, the solution contained no phenol. At the time indicated, a pulse of phenol was added to increase the concentration to 30 ppm (0.3 mM). The response of the phenol biosensor was large (45 units), indicating good sensitivity. A bare oxygen optode located in the same solution recorded a steady signal during this time. The signal from the phenol biosensor decreased because oxygen was consumed in the oxygenase-catalyzed degradation of phenol at the tip of the biosensor. Approximately 85 minutes after the pulse of phenol, the signal stabilized at a new steady state.

Example 6

Figure 19:
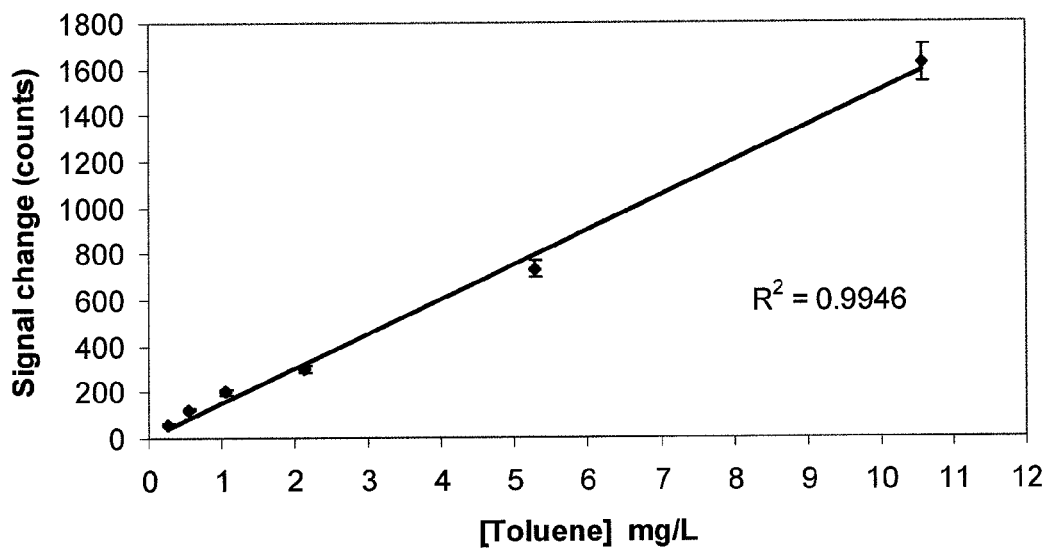
FIG. 19 depicts a calibration curve for a toluene biosensor utilizing toluene o-monooxygenase (TOM) as the biocomponent, according to an embodiment.

The enzyme toluene o-monooxygenase (TOM), expressed by a strain of *Escherichia coli* bacteria carrying the TOM genes on a plasmid has been used in a biosensor. The analyte was toluene, and the sensor was tested on aqueous solutions containing 1-10 mg/L toluene. As shown in FIG. 19, a linear relationship between the aqueous toluene concentration and the change in the intensity of the emitted fluorescent light was obtained.

Example 7

DNA shuffling is used to generate monooxygenases with differing specificities (reaction rates) toward each of six chlorinated ethenes (PCE, TCE, three DCEs and VC). A set of bacteria, each containing one of these modified monooxygenases, is used to create a set of biosensors, the signals of which can be used to resolve individual concentrations of analytes within a mixture.

In the family of seven monooxygenases (Table 8), each enzyme is encoded by six open-reading frames that give rise to an active monooxygenase. These six genes code for a hydroxylase (dimer of three proteins that contains two active sites that each hold the binuclear, oxygen-bridged iron cluster, Fe—O—Fe), reductase (~40 KDa, which transfers two electrons from NADH), small coupling protein (~16 KDa), and either a 12.5 KDa Rieske-type ferredoxin (tbuB of T3MO, touC of ToMO, and tmoC of T4MO) or a 11 KDa protein whose function is not known, but which has recently been suggested to insert iron into the hydroxylase apoenzyme (Powlowski, J., J. Sealy, V. Shingler, and E. Cadieux, "On the Role of DmpK, and Auxiliary Protein Associated with Multicomponent Phenol Hydroxylase from *Pseudomonas* sp. strain CF600," *Journal of Biological Chemistry*, 1997. 272: pp. 945-951).

Random mutagenesis for enhanced PCE, DCE and VC degradation is initiated using vector pBSKan-ToMO (8983 bp) with the complete, wild-type tou locus expressed constitutively in the stable pBSKan vector (4139 bp), since this monooxygenase is the only one with known activity for PCE. The pBSKan-ToMO vector is purified with Qiagen MIDI prep kits, and the touABCDEF genes, which encode the complete ToMO, are amplified using PCR. Shuffling then proceeds by DNase treatment of the isolated touABCDEF locus and recovery of smaller than 50 bp fragments using Centr-Sep columns. The original DNA fragments are re-built using high-fidelity Pfu polymerase (so that most of the introduced errors are from mismatches during annealing rather than from polymerase error), deoxyribonucleotides and thermal cycling without oligos for about 40 cycles. After checking for a smear of size approximately the same as ToMO via gel electrophoresis, re-assembly PCR is conducted using oligo primers containing the built-in restriction sites KpnI and NotI and designed to produce the touABCDEF locus. The resulting reassembly DNA is viewed using horizontal gel electrophoresis, purified with an ethanol/phenol/chloroform extraction, digested with KpnI and NotI, and ligated into the purified pBSKan-ToMO vector with the wild-type touABCDEF path removed. The ligated plasmids with shuffled variants are cleaned with butanol and electroporated into *E. coli* TG1 using a Bio-Rad Gene Pulser. Electroporation of *E. coli* TG1 with plasmids containing the shuffled touABCDEF locus yields about 100 colonies per plate after incubation for 16 hr at 37° C. Colonies expressing active ToMO are distinguished based on their blue color on LB plates.

The variant monooxygenases are screened using live cells by detecting the final product of chlorinated ethene degradation, chloride, measured spectrophotometrically by the procedure of Bergmann and Sanik modified for use in a 96-well plate format (Canada, K. A., S. Iwashita, H. Shim, and T. K. Wood, "Directed Evolution of Toluene ortho-Monooxygenase for Enhanced 1-Naphthol Synthesis and Chlorinated Ethene Degradation," *Journal Bacteriology*, 2002. 184: pp. 344-349). Bacteria from wells with the highest signals are saved, re-checked on additional 96-well plates, and the plasmids isolated from the highest-expressing strains used for subsequent rounds of shuffling as well as DNA sequencing. In this way, enzymes are generated that are specific for individual chlorinated ethenes (e.g., PCE, DCE, VC).

Molecular breeding (combining similar genes from different bacteria) (Minshull, 1999) may be conducted in the manner described above using the seven monooxygenase operons available in TABLE 9 in order to find variants with enhanced rates for specific chlorinated ethenes. Shuffling proceeds as described above except seven monooxygenase loci are shuffled at once rather than just ToMO; screening proceeds as for shuffling of the individual ToMO. This method introduces greater genetic diversity and can lead to even larger increases in enzymatic activity (Minshull, 1999).

TABLE 9

Family of similar monooxygenases for DNA shuffling.

| Monooxygenase | Bacterium | Locus | Fe—O—Fe cofactor |
|---|---|---|---|
| soluble methane monooxygenase (sMMO) | *M. trichosporium* OB3b | mmoXYBZY'C [78] | Present [79] |
| soluble methane monooxygenase (sMMO) | *M. capsulatus* Bath | mmoXYBZY'C [80] | Present [81] |
| toluene-o-monooxygenase (TOM) | *B. cepacia* G4 | tomA0A1A2A3A4A5 [82] | Present [83] |
| toluene/xylene-o-monooxygenase (ToMO) | *P. stutzeri* OX1 | TouABCDEF [84] | Present [85] |
| toluene-p-monooxygenase (T4MO) | *P. mendocina* KR1 | TmoABCDEF [86] | Present [83, 87] |
| toluene-m-monooxygenase (T3MO) | *R. pickettii* PKO1 | tbuA1UBVA2C [88] | Present [88] |
| phenol hydroxylase (PH) | P. CF600 | DmpKLMNOP [89] | Present [83] |

Example 8

Figure 20:
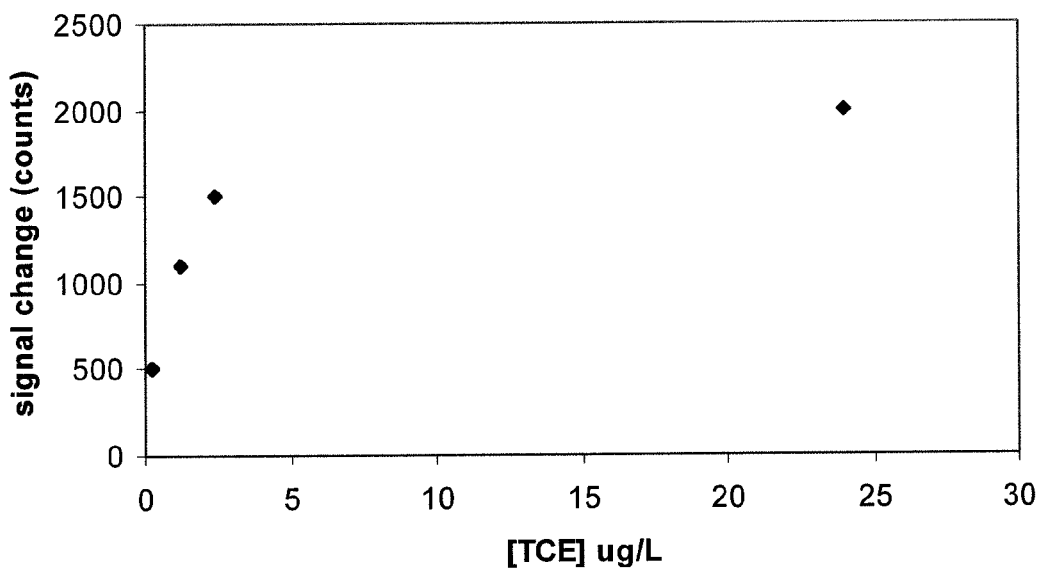
FIG. 20 depicts a calibration curve for a trichloroethene biosensor utilizing a variant of toluene o-monooxygenase (TOM-Green) as the biocomponent, according to an embodiment.

DNA shuffling and saturation mutagenesis of toluene o-monooxygenase (TOM) of *Burkholderia cepacia* G4, toluene o-xylene-monooxygenase (ToMO) of *Pseudomonas stutzeri* OX1, toluene 4-monooxygenase (T4MO) of *P. mendocina* KR1, and toluene 3-monooxygenase (T3MO) of *R. pickettii* PK01 have been performed. DNA shuffling has also been used to create the more efficient TOM-Green for the oxidation of naphthalene and the mineralization of TCE (Canada, 2002). FIG. 20 depicts a trichloroethene biosensor utilizing TOM-Green as the biocomponent.

Saturation mutagenesis was used to refine the TOM-Green enzyme to create an enzyme with three times greater activity for chloroform and a variant with two times greater naphthalene oxidation (Rui, L., Y.-M. Kwon, A. Fishman, K. F. Reardon, and T. K. Wood, "Saturation Mutagensis of Toluene ortho-Monooxygenase of *Burkholderia cepacia* G4 for Enhanced 1-Naphthol Synthesis and Chloroform Degradation," *Applied and Environmental Microbiology*, 2004. 70: pp. 3246-3252). These efforts have produced a set of enzymes that have the differential reaction rates needed for multianalyte monitoring. For example, as compared with TOM, TOM-Green is 180% faster at degrading TCE and 240% faster at degrading 1,1-DCE, but only 70% as fast at degrading toluene. And, as compared to TOM, ToMO is 1600% faster for VC and 370% faster for cis-1,2-DCE, but only 76% as fast for chloroform degradation. Enzymes of varying specificity, as illustrated by the examples for toluene and TCE in Table 10, have been produced.

TABLE 10

Reaction rates of selected monooxygenase variants produced via protein engineering

| Enzyme | Toluene oxidation rate$^a$, nmol/min/mg protein | Enzyme | Initial TCE degradation rate$^b$, nmol/min/mg protein |
|---|---|---|---|
| Wild-type ToMO | 6.1 ± 0.1 | wild-type ToMO | 0.41 ± 0.02 |
| TmoA I100S | 22.7 ± 1.6 | I100Q | 0.85 ± 0.01 |
| TmoA G103S/A107G | 1.5 ± 0.3 | K160N | 0.53 ± 0.01 |

$^a$Toluene oxidation rate determined via GC with 109 μM toluene calculated based on Henry's law.
$^b$Initial TCE degradation rates at 67 μM (actual liquid phase concentration) TCE

Example 9

The haloalkane dehalogenase LinB was used to develop biosensors for several halogenated hydrocarbons. Comparison of the sensitivity of these biosensors for two analytes with the reported activity of LinB toward those compounds (Table 11) reveals that even relatively small differences in activity—well within the range of the protein engineering—can produce significantly different biosensor sensitivities.

TABLE 11

Comparison of reported activity and biosensor sensitivity for LinB haloalkane dehalogenase.

| Analyte | LinB activity (% of 1-chlorobenzene rate)* | Biosensor sensitivity (ΔV/ppb analyte) |
|---|---|---|
| 1,2-dibromoethane | 355 | 0.29 |
| 1-chlorohexane | 145 | 0.21 |

*Damborsky, J., E. Rorije, A. Jesenska, Y. Nagata, G. Klopman, and W. J. G. M. Peijnenburg, "Structure-Specificity Relationships for Haloalkane Dehalogenases," Environ. Toxicol. Chem., 2001. 20(12): pp. 2681-2689.

Example 10

A biosensor for detecting amine-containing organic compounds has been demonstrated with the construction of a sensor for melamine (2,4,6-triamino-1,3,5-triazine). Cells of *Escherchia coli* DH5α pJS3 (Seffernick et al., J. Bact. 183 (8), 2405-2410, 2001) were immobilized in calcium alginate on the tip of an optical fiber coated with a PVA-fluoresceinamine conjugate, a pH-sensitive fluorophore. The plasmid pJS3 contains the gene triA, and thus the *E. coli* cells can express the melamine deaminase TriA, which catalyzes the cleavage of one of the amine groups. The products of this reaction are ammeline (2-hydroxy-4,6-diamino-s-triazine) and ammonia.

Figure 21A:
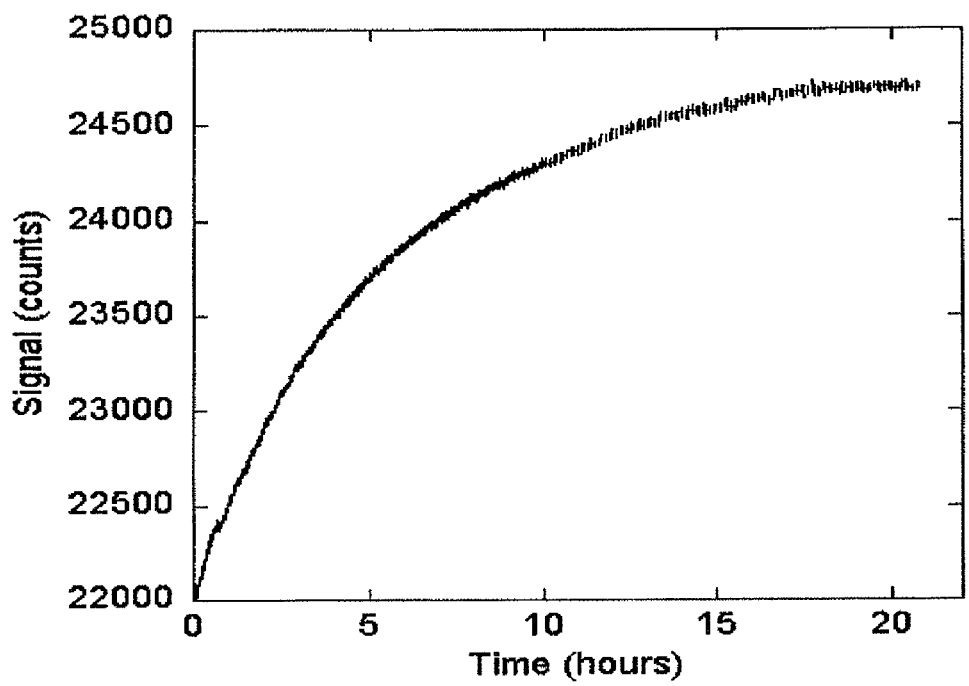
FIGS. 21A-B depict the time course of melamine biosensor response showing increased fluorescence caused by increased pH due to the release of ammonia from melamine at different concentrations.
Figure 21B:
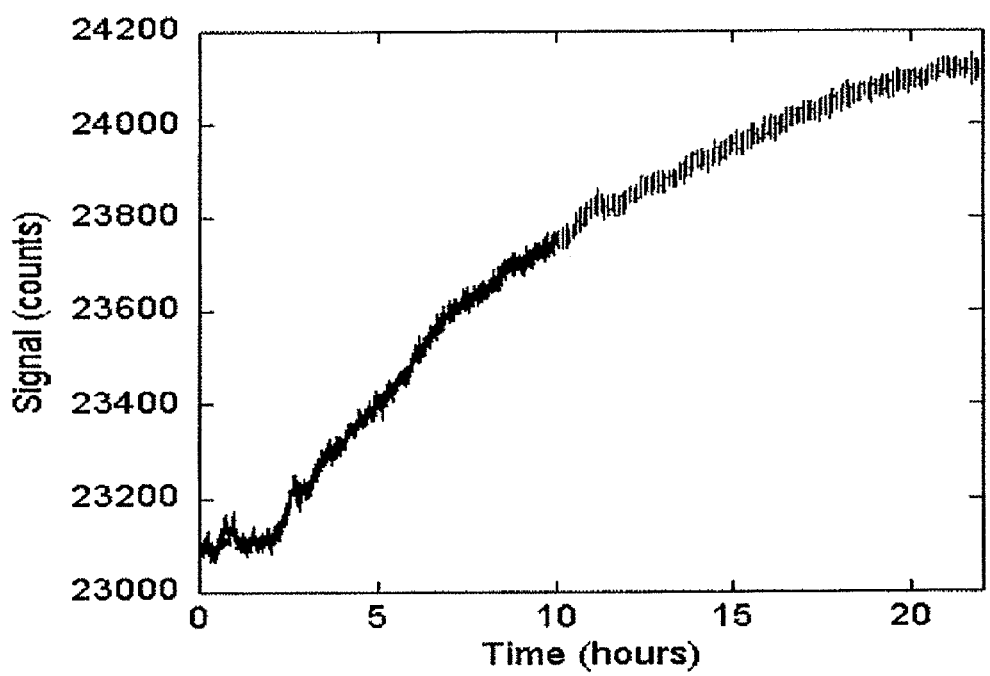

The release of ammonia led to an increase in pH on the tip of the optical fiber, which was detected as an increase in the fluorescence of fluoresceinamine (FIG. 21). FIG. 21A shows the biosensor response to 1.2 mg/L melamine. FIG. 21B shows the biosensor response to 0.12 mg/L melamine. The increases were dependent on concentration, as shown in Table 12.

Figure 22A:
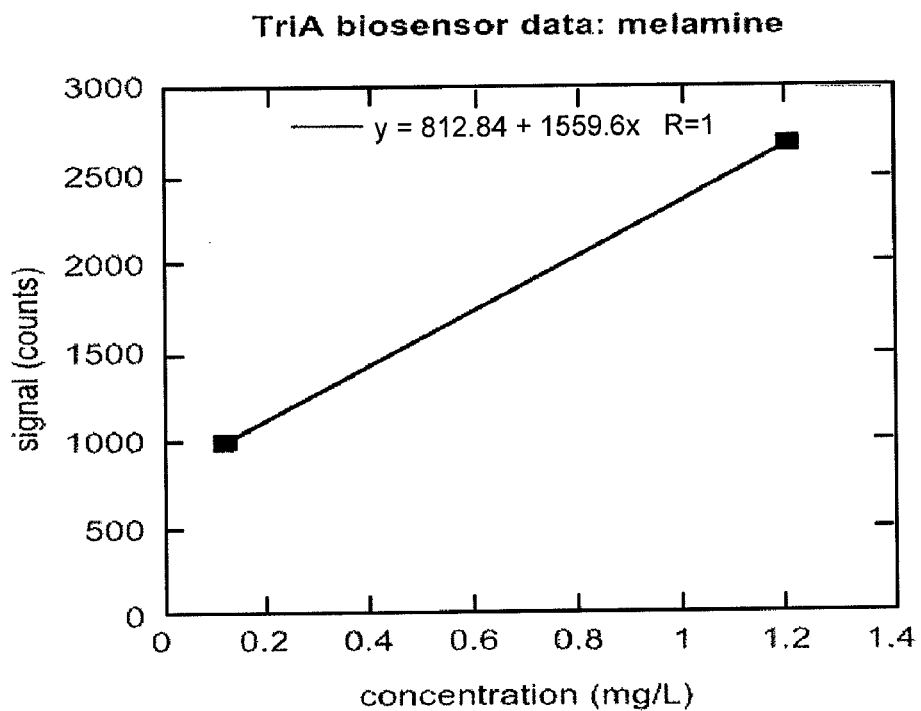
FIGS. 22A-B depict concentration-dependent responses of a melamine deaminase biosensor to melamine and 2-chloro-4,6-diamino-s-triazine (CAAT).
Figure 22B:
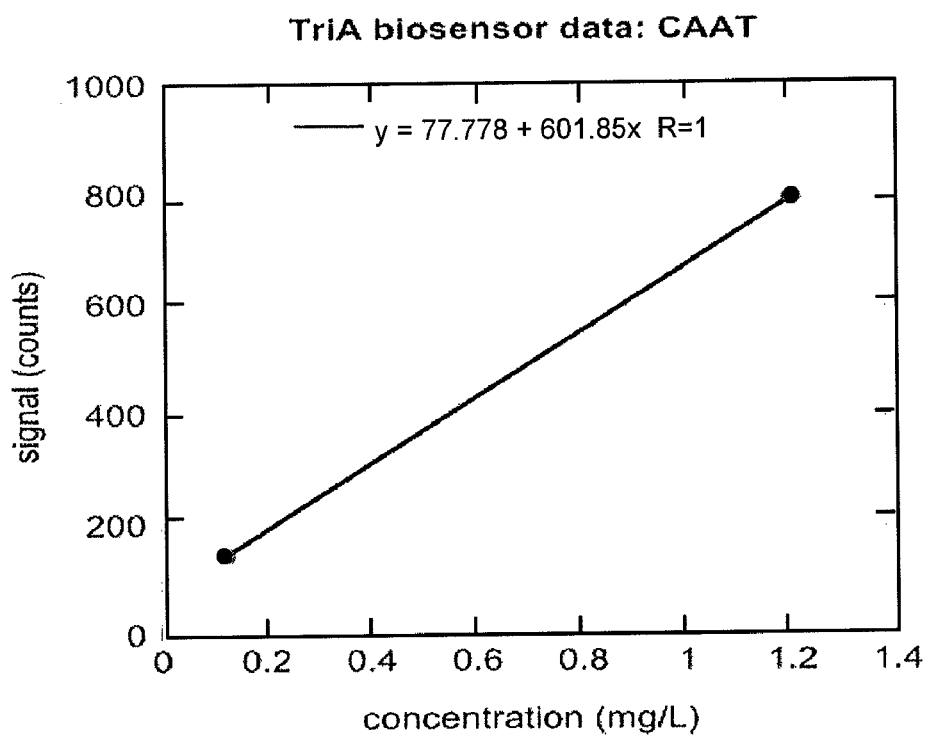

The melamine deaminase biosensor was also responsive to the related amine-containing chemical 2-chloro-4,6-diamino-s-triazine (CAAT) (Table 12 and FIG. 22). FIG. 22A shows the concentration-dependent response of the melamine deaminase biosensor to melamine. FIG. 22B shows the concentration-dependent response of the melamine deaminase biosensor to CAAT.

TABLE 12

Response of the TriA (melamine deaminase) biosensor to melamine and 2-chloro-4,6-diamino-s-triazine (CAAT).

|  | 1.21 mg/L | | 0.12 mg/L | |
| --- | --- | --- | --- | --- |
|  | Response (count) | Response time (hour) | Response (count) | Response time (hour) |
| CAAT | 800 | 10 | 150 | 2 |
| Melamine | 2700 | 16 | 1000 | 20 |

All patents, patent applications and literature publications cited in the present disclosure and/or shown in the attached list of "REFERENCES" are incorporated herein by reference in their entirety.

Changes may be made in the above systems and methods without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present systems and methods, which, as a matter of language, might be said to fall there between.

REFERENCES

[1] Heppel, L. A. and Porterfield, V. T. Enzymatic dehalogenation of certain brominated and chlorinated compounds. J. Biol. Chem. 176 (1948) 763-769.
[2] Goldman, P., Milne, G. W. A. and Keister, D. B. Carbon-halogen bond cleavage. 3. Studies on bacterial halidohydrolases. J. Biol. Chem. 243 (1968) 428-434. [Medline UI: 68123008]
[3] Motosugi, M., Esaki, N. and Soda, K. Preparation and properties of 2-halo acid dehalogenase from Pseudomonas putida. Agric. Biol. Chem. 46 (1982) 837-838.
[4] Goldman, P. The enzymatic cleavage of the carbon-fluorine bond in fluoroacetate. J. Biol. Chem. 240 (1965) 3434-3438.
[5] Goldman, P. and Milne, G. W. A. Carbon-fluorine bond cleavage. II. Studies on the mechanism of the defluorination of fluoroacetate. J. Biol. Chem. 241 (1966) 5557-5559. [Medline UI: 67053221]
[6] Chopra, I. J. and Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97. [Medline UI: 82095045]
[7] Goswani, A., Leonard, J. L. and Rosenberg, I. N. Inhibition by coumadin anticoagulants of enzymatic outer ring monodeiodination of iodothyronines. Biochem. Biophys. Res. Commun. 104 (1982) 1231-1238. [Medline UI: 82182305]
[8] Smallridge, R. C., Burman, K. D., Ward, K. E., Wartofsky, L., Dimond, R. C., Wright, F. D. and Lathan, K. R. 3',5'-Diiodothyronine to 3'-monoiodothyronine conversion in the fed and fasted rat: enzyme characteristics and evidence for two distinct 5'-deiodinases. Endocrinology 108 (1981) 2336-2345. [Medline UI: 81188610]
[9] Keuning, S., Janssen, D. B. and Witholt, B. Purification and characterization of hydrolytic haloalkane dehalogenase from Xanthobacter autotrophicus GJ10. J. Bacteriol. 163 (1985) 635-639. [Medline UI: 85261076]
[10] Scholtz, R., Leisinger, T., Suter, F. and Cook, A. M. Characterization of 1-chlorohexane halidohydrolase, a dehalogenase of wide substrate range from an Arthrobacter sp. J. Bacteriol. 169 (1987) 5016-5021. [Medline UI: 88032819]
[11] Yokota, T., Omori, T. and Kodama, T. Purification and properties of haloalkane dehalogenase from Corynebacterium sp. strain ml 5-3. J. Bacteriol. 169 (1987) 4049-4054. [Medline UI: 87307981]
[12] Muller, R., Thiele, J., Klages, U. and Lingens, F. Incorporation of [18O] water into 4-hydroxybenzoic acid in the reaction of 4-chlorobenzoate dehalogenase from Pseudomonas sp. CBS 3. Biochem. Biophys. Res. Commun. 124 (1984) 178-182. [Medline UI: 85046491]
[13] Heppel, 1948.
[14] Chang, K. H., Liang, P. H., Beck, W., Scholten, J. D., Dunaway-Mariano, D. Isolation and characterization of the three polypeptide components of 4-chlorobenzoate dehalogenase from Pseudomonas sp. strain CBS-3. Biochemistry 31 (1992) 5605-5610. [Medline UI: 92304935]
[15] Crooks, G. P., Copley, S. D. Purification and characterization of 4-chlorobenzoyl CoA dehalogenase from Arthrobacter sp. strain 4-CB1. Biochemistry, 33 (1994) 11645-11649. [Medline UI: 95001870]
[16] de Souza, M. L., Wackett, L. P., Boundy-Mills, K. L., Mandelbaum, R. T. and Sadowsky, M. J. Cloning, characterization, and expression of a gene region from Pseudomonas sp. strain ADP involved in the dechlorination of atrazine. Appl. Environ. Microbiol. 61 (1995) 3373-3378. [Medline UI: 96035669]
[17] de Souza, M. L., Sadowsky, M. J. and Wackett, L. P. Atrazine chlorohydrolase from Pseudomonas sp. strain ADP: gene sequence, enzyme purification, and protein characterization. J. Bacteriol. 178 (1996) 4894-4900. [Medline UI: 96326334]
[18] Lipke, H. and Kearns, C. W. DDT dechlorinase. I. Isolation, chemical properties, and spectrophotometric assay. J. Biol. Chem. 234 (1959) 2123-2128.
[19] Lipke, H. and Kearns, C. W. DDT dechlorinase. II. Substrate and cofactor specificity. J. Biol. Chem. 234 (1959) 2129-2132.
[20] Moorefield, H. H. Purification of DDT-dehydrochlorinase from resistant houseflies. Contr. Boyce Thompson Inst. 18 (1956) 303-310.
[21] Nagasawa, T., Ishii, T. and Yamada, H. Physiological comparison of D-cysteine desulfhydrase of Escherichia coli with 3-chloro-D-alanine dehydrochlorinase of Pseudomonas putida CR 1-1. Arch. Microbiol. 149 (1988) 413-416. [Medline UI: 88251237]
[22] Yamada, H., Nagasawa, T., Ohkishi, H., Kawakami, B. and Tani, Y. Synthesis of D-cysteine from 3-chloro-D-alanine and hydrogen sulfide by 3-chloro-D-alanine hydrogen chloride-lyase (deaminating) of Pseudomonas putida. Biochem. Biophys. Res. Commun. 100 (1981) 1104-1110. [Medline UI: 81281807]
[23] Kohler-Staub, D. and Leisinger, T. Dichloromethane dehalogenase of Hyphomicrobium sp. strain DM2. J. Bacteriol. 162 (1985) 676-681. [Medline UI: 85182487]
[24] Moriguchi, M., Hoshino, S. and Hatanaka, S.-I. Dehalogenation and deamination of 1-2-amino-4-chloro-4-pentenoic acid by Proteus mirabilis. Agric. Biol. Chem. 51 (1987) 3295.
[25] Kumagai, H., Suzuki, H., Shigematsu, H. and Tuchikura, T. S-Carboxymethylcysteine synthase from Escherichia coli. Agric. Biol. Chem. 53 (1989) 2481-2487.
[26] Hayaishi, O. Direct oxygenation by $O_2$, oxygenases. In: Boyer, P. D., Lardy, H. and Myrbäck, K. (Eds.), The Enzymes, 2nd ed., vol. 8, Academic Press, New York, 1963, p. 353-371.

[27] Junker, F., Field, J. A., Bangerter, F., Ramsteiner, K., Kohler, H.-P., Joannou, C. L., Mason, J. R., Leisinger, T. and Cook, A. M. Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. *Biochem. J.* 300 (1994) 429-436.

[28] Fujisawa, H. and Hayaishi, O. Protocatechuate 3,4-dioxygenase. I. Crystallization and characterization. *J. Biol. Chem.* 243 (1968) 2673-2681.

[29] Hayaishi, 1963.

[30] Adachi, K., Iwayama, Y., Tanioka, H. and Takeda, Y. Purification and properties of homogentisate oxygenase from *Pseudomonas fluorescens. Biochim. Biophys. Acta* 118 (1966) 88-97.

[31] Hayaishi, O. and Sutton, W. B. Enzymatic oxygen fixation into acetate concomitant with the enzymatic decarboxylation of L-lactate. *J. Am. Chem. Soc.* 79 (1957) 4809-4810.

[32] Renganathan, V. Possible involvement of toluene-2,3-dioxygenase in defluorination of 3-fluoro-substituted benzenes by toluene-degrading *Pseudomonas* sp. strain T-12. *Appl. Exp. Microbiol.* 55 (1989) 330-334.

[33] Ensley, B. D. and Gibson, D. T. Naphthalene dioxygenase: purification and properties of a terminal oxygenase component. *J. Bacteriol.* 155 (1983) 505-511.

[34] Fetzner, S., Mueller, R. and Lingens, F. Degradation of 2-chlorobenzoate by *Pseudomonas cepacia* 2CBS. *Biol. Chem. Hoppe-Seyler* 370 (1989) 1173-1182.

[35] Suzuki, K., Takemori, S. and Katagiri, M. Mechanism of the salicylate hydroxylase reaction. IV. Fluorimetric analysis of the complex formation. *Biochim. Biophys. Acta* 191 (1969) 77-85.

[36] Hosokawa, K. and Stanier, R. Y. Crystallization and properties of p-hydroxybenzoate hydroxylase from *Pseudomonas putida. J. Biol. Chem.* 241 (1966) 2453-2460.

[37] Nakagawa, H. and Takeda, Y. Phenol hydroxylase. *Biochim. Biophys. Acta* 62 (1962) 423-426.

[38] Ziegler, D. M. and Pettit, F. H. Microsomal oxidases. I. The isolation and dialkylarylamine oxygenase activity of pork liver microsomes. Biochemistry 5 (1966) 2932-2938.

[39] Colby, J. Stirling, D. I. and Dalton, H. The soluble methane mono-oxygenase of *Methylococcus capsulatus* (Bath). Its ability to oxygenate n-alkanes, n-alkenes, ethers, and alicyclic, aromatic and heterocyclic compounds. *Biochem. J.* 165 (1977) 395-402.

[40] Schenk, T., Müller, R., Mörsberger, F., Otto, M. K. and Lingens, F. Enzymatic dehalogenation of pentachlorophenol by extracts from *Arthrobacter* sp. strain ATCC 33790. *J. Bacteriol.* 171 (1989) 5487-5491.

[41] Cardini, G. and Jurtshuk, P. The enzymatic hydroxylation of n-octane by *Corynebacterium* sp. strain 7E1C. *J. Biol. Chem.* 245 (1970) 2789-2796.

[42] Augusteyn, R. C., de Jersey, J., Webb, E. C. and Zerner, B. On the homology of the active-site peptides of liver carboxylesterases. *Biochim. Biophys. Acta* 171 (1969) 128-137.

[43] Dodgson, K. S., Spencer, B. and Williams, K. Studies on sulphatases. 13. The hydrolysis of substituted phenyl sulphates by the arylsulphatase of *Alcaligenes metacaligenes. Biochem. J.* 64 (1956) 216-221.

[44] Dodgson, K. S. Glycosulphatase: observations on the activity of partially purified preparations towards the sulphate esters of certain monosaccharides and steroids. *Biochem. J.* 78 (1961) 324-333.

[45] Epstein, E. H. and Leventhal, M. E. Steroid sulfatase of human leukocytes and epidermis and the diagnosis of recessive X-linked ichthyosis. *J. Clin. Invest.* 67 (1981) 1257-1262.

[46] Takebe, I. Isolation and characterization of a new enzyme choline sulfatase. *J. Biochem. (Tokyo)* 50 (1961) 245-255.

[47] Takahashi, N. and Egami, F. Hydrolysis of polysaccharide sulphate esters by a sulphatase preparation from *Charonia lampas. Biochem. J.* 80 (1961) 384-386.

[48] Mehl, E. and Jatzkewitz, H. A cerebrosidesulfatase from swine kidney. *Hoppe-Seyler's Z. Physiol. Chem.* 339 (1964) 260-276.

[49] Farooqui, A. A. The desulphation of hexosamine sulphates by arylsulphatase B. *Experientia* 32 (1976) 1242-1244.

[50] Archer, I. M., Harper, P. S. and Wusteman, F. S. Multiple forms of iduronate 2-sulphate sulphatase in human tissues and body fluids. *Biochim. Biophys. Acta* 708 (1982) 134-140.

[51] Basner, R., Kresse, H. and von Figura, K. N-Acetylglucosamine-6-sulfate sulfatase from human urine. *J. Biol. Chem.* 254 (1979) 1151-1158.

[52] Bruce, J. S., McLean, M. W., Long, W. F. and Williamson, F. B. *Flavobacterium heparinum* 3-O-sulphatase for N-substituted glucosamine 3-O-sulphate. *Eur. J. Biochem.* 148 (1985) 359-365.

[53] Ghisalba, O. and Küenzi, M. Biodegradation and utilization of monomethyl sulfate by specialized methylotrophs. *Experientia* 39 (1983) 1257-1263.

[54] Shaklee, P. N., Glaser, J. H. and Conrad, H. E. A sulfatase specific for glucuronic acid 2-sulfate residues in glycosaminoglycans. *J. Biol. Chem.* 260 (1985) 9146-9149.

[55] Aldridge, W. N. Serum esterases. I. Two types of esterase (A and B) hydrolysing p-nitrophenyl acetate, propionate and butyrate and a method for their determination. *Biochem. J.* 53 (1953) 110-117.

[56] Augustinsson, K.-B. and Heimburger, G. Enzymatic hydrolysis of organophosphorus compounds. I. Occurrence of enzymes hydrolysing dimethyl-amido-ethoxyphosphoryl cyanide (Tabun). *Acta Chem. Scand.* 8 (1954) 753-761.

[57] Halpern, Y. S. and Grossowicz, N. Hydrolysis of amides by extracts from mycobacteria. *Biochem. J.* 65 (1957) 716-720.

[58] Kung, H.-F. and Wagner, C. γ-Glutamylmethylamide. A new intermediate in the metabolism of methylamine. *J. Biol. Chem.* 244 (1969) 4136-4140.

[59] Meister, A., Levintow, L., Greenfield, R. E. and Abendschein, P. A. Hydrolysis and transfer reactions catalyzed by ω-amidase preparations. *J. Biol. Chem.* 215 (1955) 441-460.

[60] Bray, H. G., James, S. P., Raffan, I. M., Ryman, B. E. and Thorpe, W. V. The fate of certain organic acids and amides in the rabbit. 7. An amidase of rabbit liver. *Biochem. J.* 44 (1949) 618-625.

[61] Dixon, N. E., Gazzola, C., Blakeley, R. L. and Zerner, B. Metal ions in enzymes using ammonia or amides. *Science* 191 (1976) 1144-1150.

[62] Sakaguchi, K. and Murao, S. A preliminary report on a new enzyme, "penicillin-amidase". *J. Agric. Chem. Soc. Jpn.* 23 (1950) 411.

[63] Knappe, J., Brümer, W. and Biederbick, K. Reinigung und Eigenschaften der Biotinidase aus Schweinenieren und *Lactobacillus casei. Biochem. Z.* 338 (1963) 599-613.

[64] Petrack, B., Greengard, P., Craston, A. and Sheppy, F. Nicotinamide deamidase from mammalian liver. *J. Biol. Chem.* 240 (1965) 1725-1730.

[65] Domnas, A. and Catimo, E. C. The behavior of amidohydrolases and L-glutamate in synchronized populations of *Blastocladiella emeronii. Phytochemistry* 4 (1965) 273-284.

[66] Hayaishi, O. and Kornberg, A. Metabolism of cytosine, thymine, uracil, and barbituric acid by bacterial enzymes. *J. Biol. Chem.* 197 (1952) 717-723.

[67] Florkin, M. and Duchateau-Bosson, G. Microdosage photométrique de l'allantoïne en solutions pures et dans l'urine. *Enzymologia* 9 (1940) 5-9.

[68] Citri, N. Penicillinase and other β-lactamases, in Boyer, P. D. (Ed.), *The Enzymes,* 3rd edn., vol. 4, Academic Press, New York, 1971, pp. 23-46.

[69] Tsuru, D., Oka, I. and Yoshimoto, T. Creatinine decomposing enzymes in *Pseudomonas putida. Agric. Biol. Chem.* 40 (1976) 1011-1018.

[70] Eaton, R. W. and Karns, J. S. Cloning and comparison of the DNA encoding ammelide aminohydrolase and cyanuric acid amidohydrolase from three s-triazine-degrading bacterial strains. *J. Bacteriol.* 173 (1991) 1363-1366.

[71] Ellfolk, N. Studies on aspartase. 1. Quantitative separation of aspartase from bacterial cells, and its partial purification. *Acta Chem. Scand.* 7 (1953) 824-830.

[72] Koukol, J. and Conn, E. E. The metabolism of aromatic compounds in higher plants. IV. Purification and properties of the phenylalanine deaminase of *Hordeum vulgare. J. Biol. Chem.* 236 (1961) 2692-2698.

[73] Bradbeer, C. The clostridial fermentations of choline and ethanolamine. 1. Preparation and properties of cell-free extracts. *J. Biol. Chem.* 240 (1965) 4669-4474.

[74] Katapodis, A. G., Ping, D. and May, S. W. A novel enzyme from bovine neurointermediate pituitary catalyzes dealkylation of α-hydroxyglycine derivatives, thereby functioning sequentially with peptidylglycine α-amidating monooxygenase in peptide amidation. *Biochemistry* 29 (1990) 6115-6120.

[75] Asano, N., Takeuchi, M., Ninomiya, K., Kameda, Y. and Matsui, K. Microbial degradation of validamycin A by *Flavobacterium saccharophilum*. Enzymatic cleavage of C—N linkage in validoxylamine A. *J. Antibiot.* 37 (1984) 859-867.

[76] Treimer, J. K. and Zenk, M. H. Purification and properties of strictosidine synthase, the key enzyme in indole alkaloid formation. *Eur. J. Biochem.* 101 (1979) 225-233.

[77] DeEknamkul, W., Ounaroon, A., Tanahashi, T., Kutchan, T. and Zenk, M. H. Enzymatic condensation of dopamine and secologanin by cell-free extracts of *Alangium lamarckii*. *Phytochemistry* 45 (1997) 477-484.

[78] Cardy, D. L. N., V. Laidler, G. P. C. Salmond, and J. C. Murrell, "Molecular Analysis of the Methane Monooxygenase (MMO) Gene Cluster of *Methylosinus trichosporium* OB3b," *Molecular Microbiology*, 1991. 5 (2): pp. 335-342.

[79] Fox, 1989.

[80] Stainthorpe, A. C., V. Lees, G. P. C. Salmond, H. Dalton, and J. C. Murrell, "The Methane Monooxygenase Gene Cluster of *Methylococcus capsulatus* (Bath)," *Gene,* 1990. 91: pp. 27-34.

[81] Rosenzwieg, A. C., P. Nordlund, P. M. Takahara, C. A. Frederick, and S. J. Lippard, "Geometry of the Soluble Methane Monooxygenase Catalytic Diiron Center in Two Oxidation States," *Chemistry and Biology*, 1995. 2 (6): pp. 409-418.

[82] Shields, M. S. and S. C. Francesconi, Microbial Degradation of Trichloroethylene, Dichloroethylene, and Aromatic Pollutants, in U.S. Pat. No. 5,543,317. 1996.

[83] Newman, 1995.

[84] Bertoni, G., F. Bolognese, E. Galli, and P. Barbieri, "Cloning of the Genes for and Characterization of the Early Stages of Toluene and o-Xylene Catabolism in *Pseudomonas stutzeri* OX1," *Applied and Environmental Microbiology*, 1996, 62 (10): pp. 3704-3711

[85] Bertoni, G., M. Martino, E. Galli, and P. Barbieri, "Analysis of the Gene Cluster Encoding Toluene/o-Xylene Monooxygenase from *Pseudomonas stutzeri* OX1,"*Applied and Environmental Microbiology,* 1998. 64 (10): pp. 3626-3632.

[86] Pikus, J. D., J. M. Studts, C. Achim, K. E. Kauffmann, E. Munck, R. J. Steffan, K. McClay, and B. G. Fox, "Recombinant Toluene-4-Monoxygenase: Catalytic and Mossbauer Studies of the Purified Diiron and Rieski Components of a Four-Protein Complex," *Biochemistry,* 1996. 35: pp. 9106-9119; Yen, K.-M., "Construction of Cloning Cartridges for Development of Expression Vectors in Gram-Negative Bacteria," *J. Bacteriol,* 1991. 173 (17): pp. 5328-5335.

[87] Newman, 1995; McClay, K., B. G. Fox, and R. J. Steffan, "Chloroform Mineralization by Toluene-Oxidizing Bacteria," *Applied and Environmental Microbiology,* 1996. 62 (8): pp. 2716-2722.

[88] Byrne, A. M., J. J. Kukor, and R. H. Olsen, "Sequence Analysis of the Gene Cluster Encoding Toluene-3-monooxygenase from *Pseudomonas pickettii* PK01," *Gene,* 1995.154: pp. 65-70.

[89] Nordlund, I., J. Powlowski, and V. Shingler, "Complete nucleotide sequence and polypeptide analysis of multicomponent phenol hydroxylase from *Pseudomonas* sp. strain CF600," *Journal of Bacteriology,* 1990. 172: pp. 6826-6833.

What is claimed is:

1. A distal tip of a biosensor transducer for use in detecting an organic compound susceptible to deamination, the tip comprising:
   a biocomponent comprising one or more enzymes for carrying out deamination of the organic compound, said biocomponent immobilized to a surface of the tip by one or more of (a) entrapment within a hydrogel; (b) entrapment within a polymeric network; (c) encapsulation; (d) covalent bonding; and (e) adsorption;
   wherein said biocomponent has been treated to maintain a period of enzymatic efficacy; and
   wherein said biocomponent is stabilized to said tip by one or more of crosslinking a surface of said immobilized biocomponent, crosslinking a polymer layer to said biocomponent, adding a gel-hardening agent to said biocomponent, adding a stabilizing agent to said biocomponent, and modifying a component used to immobilize said biocomponent to said surface of the tip.

2. The distal tip of claim 1, wherein the biosensor transducer is selected from the group consisting of an optical transducer, a pH optode, a pH electrode, a field-effect transistor (FET) and an ion-selective electrode (ISE).

3. The distal tip of claim 1, the one or more enzymes selected from hydrolases of subclass EC 3.5 and lyases of subclass EC 4.3.

4. The distal tip of claim 1, wherein said biocomponent is treated according to a treatment selected from the group consisting of applying an inhibitor of protein synthesis, adding a protease inhibitor, freeze drying and dry heating.

5. The distal tip of claim 1, wherein said biocomponent is selected from whole isolated cells, purified enzymes and combinations thereof.

6. The distal tip of claim 1, wherein the organic compound is selected from the group consisting of melamine, ammeline, ammelide, serine, biotin and aniline.

7. The distal tip of claim 1, said biocomponent stabilized to said tip by crosslinking the polymer layer, wherein said crosslinked polymer layer is selected from the group consisting of poly-L-lysine, polyethylenimine, polyacrylic acid, polyvinyl alcohol, polyacrylamide and polyurethane.

8. A distal tip of a biosensor transducer for use in detecting an organic compound susceptible to deamination, the tip comprising:
   a biocomponent comprising at least one enzyme selected from the group consisting of hydrolases from EC family 3.5 and lyases from EC family 4.3 for carrying out deamination of the organic compound, said biocomponent immobilized to a surface of the tip by one or more of (a) entrapment within a hydrogel; (b) entrapment within a polymeric network; (c) encapsulation; (d) covalent-bonding; and (e) adsorption, wherein said biocomponent is stabilized to said tip by one or more of crosslinking a surface of said immobilized biocomponent, crosslinking a polymer layer to said biocomponent, adding a gel-hardening agent to said biocomponent, adding a stabilizing agent to said biocomponent, and modifying a component used to immobilize said biocomponent to said surface of the tip.

9. The distal tip of claim 8, wherein the biosensor transducer is selected from the group consisting of an optical transducer, a pH optode, a pH electrode, a field-effect transistor (FET) and an ion-selective electrode (ISE).

10. The distal tip of claim 8, wherein said biocomponent is treated according to a treatment selected from the group consisting of applying an inhibitor of protein synthesis, adding a protease inhibitor, freeze drying and dry heating.

11. The distal tip of claim 8, wherein said biocomponent is selected from whole isolated cells, purified enzymes and combinations thereof.

12. The distal tip of claim 8, wherein the organic compound is selected from the group consisting of melamine, ammeline, ammelide, serine, biotin and aniline.

13. The distal tip of claim 8, said biocomponent stabilized to said tip by crosslinking the polymer layer, wherein said crosslinked polymer layer is selected from the group consisting of poly-L-lysine, polyethylenimine, polyacrylic acid, polyvinyl alcohol, polyacrylamide and polyurethane.

14. A distal tip of a biosensor transducer for use in detecting organic compounds, the tip comprising:
a biocomponent comprising at least one enzyme selected from the group consisting of hydrolases from EC family 3.5 and lyases from EC family 4.3 for carrying out deamination of one organic compound; and
one or more of (i) an oxygenase from EC family 1.13 for carrying out an oxidation of one organic compound, (ii) an oxygenase from EC family 1.14 for carrying out an oxidation of one organic compound, (iii) a dehalogenase for carrying out dehalogenation of one organic compound, and (iv) a hydrolase from subclass EC 3.1 for carrying out hydrolysis of one organic compound, said biocomponent immobilized to a surface of the tip by one or more of (a) entrapment within a hydrogel; (b) entrapment within a polymeric network; (c) encapsulation; (d) covalent-bonding; and (e) adsorption,
wherein said biocomponent is stabilized to said tip by one or more of crosslinking a surface of said immobilized biocomponent, crosslinking a polymer layer to said biocomponent, adding a gel-hardening agent to said biocomponent, adding a stabilizing agent to said biocomponent, and modifying a component used to immobilize said biocomponent to said surface of the tip.

15. The distal tip of claim 14, further comprising a device for delivering one or more reagents.

16. The distal tip of claim 15, wherein the reagent is selected from oxygen and hydrogen peroxide.

17. The distal tip of claim 14, said biocomponent stabilized to said tip by crosslinking the polymer layer, wherein said crosslinked polymer layer is selected from the group consisting of poly-L-lysine, polyethylenimine, polyacrylic acid, polyvinyl alcohol, polyacrylamide and polyurethane.

18. The distal tip of claim 14, wherein the biosensor transducer is selected from the group consisting of an optical transducer, a pH optode, a pH electrode, a field-effect transistor (FET), an ion-selective electrode (ISE), and an oxygen optode.

19. The distal tip of claim 14, wherein the organic compound is selected from the group consisting of melamine, ammeline, ammelide, serine, biotin and aniline.

20. The distal tip of claim 14, wherein said biocomponent is treated according to a treatment selected from the group consisting of applying an inhibitor of protein synthesis, adding a protease inhibitor, freeze drying and dry heating.

\* \* \* \* \*

UNITED STATES PATENT AND TRADEMARK OFFICE
CERTIFICATE OF CORRECTION

PATENT NO. : 8,323,956 B2
APPLICATION NO. : 12/358140
DATED : December 4, 2012
INVENTOR(S) : Kenneth F. Reardon et al.

It is certified that error appears in the above-identified patent and that said Letters Patent is hereby corrected as shown below:

Title page, Item (73) Assignee, "Colorado State University Research Foundation, Fort Collins, CO (US)" should read -- Colorado State University Research Foundation, Fort Collins, CO (US) and Regents of the University Of Minnesota, Saint Paul, Minnesota (US) --

Signed and Sealed this
Fifth Day of August, 2014

Michelle K. Lee
*Deputy Director of the United States Patent and Trademark Office*